(12) United States Patent
Popp et al.

(10) Patent No.: US 7,829,107 B2
(45) Date of Patent: Nov. 9, 2010

(54) FOAMABLE PHARMACEUTICAL COMPOSITIONS AND METHODS FOR TREATING A DISORDER

(75) Inventors: Karl F. Popp, Schodack Landing, NY (US); Edward R. Yuhas, Yonkers, NY (US)

(73) Assignee: Stiefel Laboratories, Inc., Coral Gables, FL (US)

( * ) Notice: Subject to any disclaimer, the term of this patent is extended or adjusted under 35 U.S.C. 154(b) by 1031 days.

(21) Appl. No.: 11/595,864

(22) Filed: Nov. 13, 2006

(65) Prior Publication Data

US 2007/0059253 A1 Mar. 15, 2007

Related U.S. Application Data

(62) Division of application No. 10/445,487, filed on May 28, 2003, now Pat. No. 7,186,416.

(51) Int. Cl.
*A61K 7/00* (2006.01)
*A61K 7/48* (2006.01)
*A61K 9/12* (2006.01)
*A61K 31/57* (2006.01)

(52) U.S. Cl. .................. 424/401; 424/45; 424/78.03; 424/78.06; 514/861; 514/863

(58) Field of Classification Search ................. 424/401, 424/45, 78.03, 78.06; 514/861, 863
See application file for complete search history.

(56) References Cited

U.S. PATENT DOCUMENTS

| | | | |
|---|---|---|---|
| 4,018,918 A | 4/1977 | Ayer et al. | |
| 4,141,417 A | 2/1979 | Schora et al. | |
| 4,141,472 A * | 2/1979 | Spitzer et al. ......... | 222/189.01 |
| 4,420,484 A | 12/1983 | Gorman et al. | |
| 4,806,262 A | 2/1989 | Snyder | |
| 4,847,068 A | 7/1989 | Dole et al. | |
| 4,882,182 A | 11/1989 | Halls et al. | |
| 4,885,354 A | 12/1989 | Hofer et al. | |
| 4,915,934 A | 4/1990 | Tomlinson | |
| 4,981,678 A | 1/1991 | Tomlinson | |
| 5,002,680 A | 3/1991 | Schmidt et al. | |
| 5,110,809 A | 5/1992 | Wang et al. | |
| 5,143,717 A | 9/1992 | Davis | |
| 5,167,950 A | 12/1992 | Lins | |
| 5,352,437 A | 10/1994 | Nakagawa et al. | |
| 5,397,564 A | 3/1995 | Seki et al. | |
| 5,446,028 A * | 8/1995 | Klein et al. ................... | 514/43 |
| 5,516,504 A | 5/1996 | Tomlinson | |
| 5,679,324 A | 10/1997 | Lisboa et al. | |
| 5,684,044 A | 11/1997 | Yu et al. | |
| 5,733,558 A | 3/1998 | Breton et al. | |
| RE35,843 E | 7/1998 | Diamond et al. | |
| 5,776,430 A | 7/1998 | Osborne et al. | |
| 5,783,202 A | 7/1998 | Tomlinson et al. | |
| 5,788,155 A | 8/1998 | Martin et al. | |
| 5,833,960 A | 11/1998 | Gers-Barlag et al. | |
| 5,935,554 A | 8/1999 | Tonlinson | |
| 6,030,931 A | 2/2000 | Vinski et al. | |
| 6,060,085 A | 5/2000 | Osborne | |
| 6,126,920 A | 10/2000 | Jones et al. | |
| 6,211,250 B1 | 4/2001 | Tomlinson et al. | |
| 6,231,835 B1 | 5/2001 | Kimura | |
| 6,231,875 B1 | 5/2001 | Sun et al. | |
| 6,253,762 B1 | 7/2001 | Britto | |
| 6,264,964 B1 | 7/2001 | Mohammadi | |
| 6,267,949 B1 | 7/2001 | Halls | |
| 6,284,234 B1 | 9/2001 | Niemiec et al. | |
| 6,383,471 B1 | 5/2002 | Chen et al. | |
| 6,419,913 B1 | 7/2002 | Niemiec et al. | |
| 6,547,063 B1 | 4/2003 | Zaveri et al. | |
| 6,730,288 B1 | 5/2004 | Abram | |
| 2003/0113385 A1 | 6/2003 | Schleicher et al. | |
| 2003/0118511 A1 | 6/2003 | Jones et al. | |
| 2004/0151671 A1 | 8/2004 | Abram et al. | |

FOREIGN PATENT DOCUMENTS

EP 0331489 A2 9/1989

(Continued)

OTHER PUBLICATIONS

Woodford et al., "Bioavailability and activity of topical corticosteroids from a novel drug delivery system, the aerosol quick-break foam" (Abstract), *J. Pharm. Sci.*, 1977, 66(1), 99-103.

(Continued)

*Primary Examiner*—Mina Haghighatian
(74) *Attorney, Agent, or Firm*—The Nath Law Group; Joshua B. Goldberg; Charles D. Niebylski

(57) ABSTRACT

Novel compositions of matter comprising a foamable delivery system are provided. Novel methods for treating a disease, disorder, or condition using the novel compositions are further provided. Novel methods for making and delivering a foamable pharmaceutical composition are also provided. While the novel compositions and foamable drug delivery system may be utilized for administration of a wide variety of drugs to epithelial tissues, to treat a wide variety of diseases, disorders, or conditions, the inventive compositions and foamable drug delivery systems are particularly useful for the dermatological administration of corticosteroids and antifungal agents.

23 Claims, No Drawings

FOREIGN PATENT DOCUMENTS

| | | |
|---|---|---|
| EP | 0423695 A3 | 4/1991 |
| EP | 0484530 A1 | 5/1992 |
| EP | 0 535 327 A1 | 4/1993 |
| EP | 0813413 B1 | 12/1997 |
| EP | 1070752 A2 | 1/2001 |
| FR | 2677369 | 12/1992 |
| FR | 2 820 038 | 8/2002 |
| GB | 2327344 | 1/1999 |
| WO | WO 85/01876 | 5/1985 |
| WO | WO 86/00196 | 1/1986 |
| WO | WO 88/04896 | 7/1988 |
| WO | WO 92/04419 | 3/1992 |
| WO | WO 93/25189 | 12/1993 |
| WO | WO 94/16732 | 8/1994 |
| WO | WO 96/27376 | 9/1996 |
| WO | WO 97/17075 | 5/1997 |
| WO | WO 98/23291 | 6/1998 |
| WO | WO 98/52525 | 11/1998 |
| WO | WO 99/04751 | 2/1999 |
| WO | WO 99/20250 | 4/1999 |
| WO | WO 99/53923 | 10/1999 |
| WO | WO 00/15193 | 3/2000 |
| WO | WO 00/66172 | 11/2000 |
| WO | WO 03/039559 A1 | 5/2003 |

OTHER PUBLICATIONS

"Quick-Breaking Foam Aerosols", *Aerosol Age*, May 1960.
Gennaro, A.R. "Remington: The Science and Practice of Pharmacy", Chapter 17, vol. II pp. 225-230.
PDR® entry for LUXIQ® (Connetics) (betamethasone valerate).

* cited by examiner

FOAMABLE PHARMACEUTICAL COMPOSITIONS AND METHODS FOR TREATING A DISORDER

This application is a divisional application of U.S. Ser. No. 10/445,487, filed May 28, 2003 now U.S. Pat. No. 7,186,416.

BACKGROUND OF THE INVENTION

1. Field of Invention

The present inventive subject matter relates to novel foamable delivery systems. The present inventive subject matter further relates to pharmaceutical compositions and methods for treating a disease, disorder, or condition using the inventive delivery systems. The present inventive subject matter further relates to methods for making and methods for delivering a foamable pharmaceutical composition. While these foamable drug delivery systems may be utilized for administration of a wide variety of drugs to epithelial tissues to treat a wide variety of diseases, disorders, or conditions, the inventive foamable drug delivery systems are particularly useful for treating diseases affecting mammalian skin and mucous membranes by application or instillation of a pharmaceutically active agent that can modify the appearance, metabolic or functional state, permeability, and/or health of a living organism.

2. Background

Foamable dosage forms are known in the art generally as suitable for topical application to mammals. However, foams are further known as a volatile dosage form that do not exhibit a great deal of stability.

Foam Stability

Foams are thermodynamically unstable systems. Since the total surface area in a foam is large, there is a considerable amount of surface energy present. Accordingly, a surface active agent is necessary to achieve any reasonable degree of stability so the foam can last for a reasonable amount of time.

Good emulsifying agents are, in general, also good foaming agents, since the factors influencing emulsion stability against droplet coalescence and foam stability against bubble collapse are similar. The stability of a foam depends upon three principal factors: (1) the tendency for liquid films to drain and become thinner; (2) the tendency of foam bubbles to rupture as a result of random disturbances; and (3) change in bubble size. Other factors which may significantly influence foam stability include evaporation and gas diffusion through the liquid films.

Foam Drainage

Initially, foam drainage takes place mainly by gravitational flow, allowing the spheres of gas in the foam to become closer together. Foaming agents play an important role at this stage in restricting gravitational flow to a level where local disturbances and consequent film rupture is minimized.

When the films between the gas spheres have attained a thickness on the order of micrometers, gravitational flow becomes extremely slow. When the bubble wall becomes sufficiently thin to be permeable, the gas in the smaller bubbles diffuses into adjacent bubbles to equalize the pressure and produce larger bubbles. This spontaneous process increases the average bubble size without film rupture. The predominant drainage mechanism then involves liquid being discharged locally via capillary action at positions of interfilm contact known as Plateau borders, where the liquid capacity is relatively high, existing throughout the foam. The final, stable equilibrium product is a fragile, honeycomb structure, in which the separating films have plane surfaces.

Foam drainage causes the liquid films separating the gas bubbles to become thinner. This usually leads to film rupture.

Film Rupture

In addition to film drainage, the stability of a film depends on the ability of the liquid film to resist excessive local thinning and rupture occurring as a result of random disturbances. A number of factors may be involved with varying degrees of importance, depending on the nature of the particular foam in question.

For example, when a film is subjected to local stretching as a result of some external disturbance, the consequent increase in surface area will be accompanied by a decrease in the surface excess concentration of foaming agent and a resulting local increase in surface tension. A certain time is required for surfactant molecules to diffuse to this surface region and restore the original surface tension. This increased surface tension may persist for long enough to cause the disturbed film region to recover its original thickness, stabilizing the foam.

The stress that creates regions of higher surface tension is always present in a foam film. The liquid film is flat at one place and curved convexly at another, where the liquid accumulates in the interstices between the bubbles. The convex curvature creates a capillary force, called the Laplace effect, that sucks liquid out of connected foam films so that internal liquid flows constantly from the flatter to the more curved parts of the films. As the liquid flows, the films are stretched, new surfaces of higher tension are created, and a counter-flow across the surfaces is generated to restore the thinned-out parts of the films, a process called the Marangoni effect. In this way, the foam films are in a constant state of flow and counterflow, one effect creating the conditions for its reversal by the other.

Rupture of the liquid films separating the bubbles leads to coalescence of the bubbles and complete collapse of the foam structure.

Changes in Bubble Size

Change in bubble size can lead to thinning of the lamellae and may cause mechanical shocks that result in film rupture. As a foam ages, the small bubbles become smaller and the large bubbles grow larger. This occurs because the pressure in a small bubble is higher than that in large bubbles. The difference in pressure between the two bubbles increases until the smaller bubble disappears completely. The resulting rearrangement of the bubbles in the foam could lead to an increased possibility of mechanical shock followed by film rupture and coalescence.

Surface Rheology

Rheology is the science of deformation and flow of matter. The mechanical properties of the surface films of a foam have a considerable influence on foam stability. First, high bulk liquid viscosity retards the rate of foam collapse. However, high surface viscosity also produces strong retardation of bulk liquid flow close to the surfaces and, consequently, the drainage of thick films is considerably more rapid than that of thin films, which facilitates the attainment of a uniform film thickness. Second, surface elasticity facilitates the maintenance of a uniform film thickness. However, the existence of rigid, condensed surface films is detrimental to foam stability, owing to the very small changes in area over which such films show elasticity.

A number of U.S. patents have previously been granted disclosing the use of foams and mousses as pharmaceutical or cosmetic compositions, as drug delivery systems, and for skin care. The majority of these patents pertain to specific formulations containing specific drugs for treating specific disorders. Representative of this body of art are the following U.S. patents.

Dole et al., U.S. Pat. No. 4,847,068, disclose a skin care composition in the form of an aerosol mousse comprising mineral oil, an emulsifier, water, and a propellant.

Schmidt et al., U.S. Pat. No. 5,002,680, disclose a skin cleansing aerosol mousse-forming emulsion comprising a concentrate, a mild non-soap anionic or amphoteric surfactant, a polymeric skin feel aid, a moisturizer which is preferably glycerin, water, and a propellant.

Lins, U.S. Pat. No. 5,167,950, discloses a high alcohol content aerosol antimicrobial mousse comprising a hydrocarbon propellant, ethanol or isopropyl alcohol, a water-dispersible polymeric gelling agent, an amphiphilic system consisting of at least one alcohol with a hydrocarbon group of from 16 to 22 carbons, and at least one nonionic surfactant.

Seki et al., U.S. Pat. No. 5,397,564, disclose an aerosol sherbet-like foam preparation for topical use, primarily for skin cooling, comprising water, a lower alcohol, liquefied petroleum gases, and dimethyl ether.

Lisboa et al., U.S. Pat. No. 5,679,324, disclose a low stinging and low burning aerosol foamable fragrance composition which forms a fast breaking foam containing a surfactant, a propellant, a fragrance, a thickener, and a cosmetic vehicle.

Vinski et al., U.S. Pat. No. 6,030,931, disclose a foaming cleansing composition free of water insoluble emollients containing an anionic surfactant and an amphoteric surfactant, packaged in a non-aerosol dispenser.

Osborne, U.S. Pat. No. 6,060,085, discloses a semisolid aqueous gel pharmaceutical composition customized for treatment of acne and herpes lesions. The composition includes a dissolved pharmaceutical that has the capacity to permeate the stratum corneum layer of the epidermis and become available systemically, and a pharmaceutical in a micro-particulate state that does not readily cross the stratum corneum of the epidermis.

Jones et al., U.S. Pat. No. 6,126,920, disclose a method of treating a skin disease with a foamable corticosteroid-containing pharmaceutical composition comprising a corticosteroid active substance; a quick-break foaming agent comprising an aliphatic alcohol, a fatty alcohol, water, and a surface active agent; a propellant; and a buffering agent.

Mohammadi, U.S. Pat. No. 6,264,964, discloses a foaming cosmetic product comprising a container with a nozzle outlet and a foaming mechanism, a crosslinked non-emulsifying polysiloxane elastomer, and a carboxyvinyl polymer.

Each of these patented formulations exhibits certain disadvantages and/or deficiencies. Accordingly, there remains a need in the art for improved formulations containing an active therapeutic agent that more effectively target epithelial cell tissue for the treatment of diseases, disorders, and conditions thereof. The present inventive subject matter addresses this need by providing, at a minimum, one of the following improvements: improved delivery of active therapeutic agent (s), decreased inconvenience and irritation, increased ease of use for the patient, and reduced degradation of the active therapeutic agent(s). Further, the present inventive subject matter may beneficially affect the appearance, metabolic or functional state, or permeability of a tissue or living organism, resulting in improvements in the health of the living organism at the expense of an antagonist thereto, such as pathogenic organisms and other disease states involving cells.

SUMMARY OF THE INVENTION

The present inventive subject matter relates to compositions comprising and methods of using a novel foamable delivery system which comprises:

(i) a solvent composition selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof;

(ii) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum derivative surfactant, an aliphatic amine surfactant, a polysiloxane derivative, a sorbitan fatty acid ester, pharmaceutically acceptable salts thereof, and mixtures thereof;

(iii) a propellant; and (iv) an acid in an amount to affect the delivery system's pH selected from the group consisting of:

(a) acetylsalicyclic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;

(b) an alpha hydroxyacid of formula I:

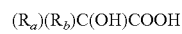

$$(R_a)(R_b)C(OH)COOH \qquad \qquad I$$

or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;

(c) an alpha ketoacid of formula II:

$$(R_a)COCOO(R_b) \qquad \qquad II$$

or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;

(d) an acid of formula III:

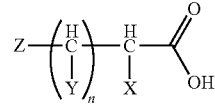

or a pharmaceutically acceptable salt, ester, or solvate thereof, wherein n is 0-6;

X is H, OH, or $NH_2$, each Y is H or OH, or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;

Z is H, $CH_3$, OH, COOH, or SH, provided that Y and Z are not both OH, or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N; and (e) mixtures thereof.

In a preferred embodiment, the present inventive subject matter relates to a pharmaceutical composition comprising:

(A) an effective amount of one or more active therapeutic agents or pharmaceutically acceptable free bases, salts, esters, or solvates thereof; and (B) a pharmaceutically acceptable carrier, comprising:
  (i) a foamable delivery system which comprises:
    (a) a solvent composition selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof; and
    (b) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum derivative surfactant, an aliphatic amine surfactant, a polysiloxane derivative, a sorbitan fatty acid ester, pharmaceutically acceptable salts thereof, and mixtures thereof;
  (ii) a propellant; and
  (iii) an acid in an amount to affect the composition's pH selected from the group consisting of:
    (a) acetylsalicyclic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;
    (b) an alpha hydroxyacid of formula I:

$(R_a)(R_b)C(OH)COOH$          I or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;

(c) an alpha ketoacid of formula II:

$(R_a)COCOO(R_b)$          II or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;

(d) an acid of formula III:

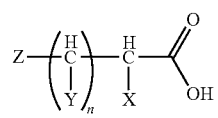

or a pharmaceutically acceptable salt, ester, or solvate thereof, wherein
    n is 0-6;
    X is H, OH, or $NH_2$,
    each Y is H or OH,
    or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;
    Z is H, $CH_3$, OH, COOH, or SH, provided that Y and Z are not both OH,
    or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N; and
    (e) mixtures thereof.

In a further preferred embodiment, the present inventive subject matter relates to a pharmaceutical composition comprising:

(A) an effective amount of one or more active therapeutic agents or pharmaceutically acceptable free bases, salts, esters, or solvates thereof; and (B) a pharmaceutically acceptable carrier, comprising:
  (i) a foamable delivery system which comprises:
    (a) a solvent composition selected from the group consisting of water, ethanol, isopropyl alcohol, benzyl alcohol, dimethyl isosorbide, propylene carbonate, xylene, methylene chloride, ethylhexanediol, polysiloxanes, dimethyl ether, and mixtures thereof; and
    (b) a surfactant composition selected from the group consisting of laureth-4, PEG-2 dilaurate, stearic acid, sodium lauryl sulfate, dioctyl sodium sulfosuccinate, cocoamphopropionate, poloxamer 188, meroxapol 258, triethanolamine, dimethicone, polysorbate 60, sorbitan monostearate, pharmaceutically acceptable salts thereof, and mixtures thereof;
  (ii) a propellant; and
  (iii) an acid in an amount to affect the composition's pH selected from the group consisting of acetic acid, acetylsalicylic acid, adipic acid, ascorbic acid, aspartic acid, benzoic acid, boric acid, carbonic acid, citric acid, formic acid, ethanesulfonic acid, fumaric acid, glycerophosphoric acid, gluconic acid, glutaric acid, glycine, glyceric acid, glycolic acid, glutamic acid, hippuric acid, hydrochloric acid, lactic acid, maleic acid, malic acid, malonic acid, mandelic acid, methanesulfonic acid, mucic acid, nitrous acid, oxalic acid, pelargonic acid, phosphoric acid, propionic acid, saccharin, salicylic acid, sorbic acid, succinic acid, sulfuric acid, tartaric acid, thioglycolic acid, thiosulfuric acid, undecylenic acid, ethanolamine, naturally and synthetically derived amino acids, derivatives thereof, and mixtures thereof.

In a yet another preferred embodiment, the present inventive subject matter relates to a pharmaceutical composition having a starting concentration of an active therapeutic agent comprising:

(A) an effective amount of one or more active therapeutic agents or pharmaceutically acceptable free bases, salts, esters, or solvates thereof; and (B) a pharmaceutically acceptable carrier, comprising:
  (i) a foamable delivery system which comprises:
    (a) a solvent composition selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof; and
    (b) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum derivative surfactant, an aliphatic amine surfactant, a polysiloxane derivative, a sorbitan fatty acid ester, pharmaceutically acceptable salts thereof, and mixtures thereof;
  (ii) a propellant; and
  (iii) an acid in an amount to affect the composition's pH selected from the group consisting of:
    (a) acetylsalicyclic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;
    (b) an alpha hydroxyacid of formula I:

$(R_a)(R_b)C(OH)COOH$  I or a pharmaceutically acceptable salt, lactone, or solvate thereof wherein $R_a$ and $R_b$ are independently selected from the group consisting of H, F, Cl, Br, 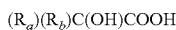 and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;
    (c) an alpha ketoacid of formula II:

$(R_a)COCOO(R_b)$  II or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;
    (d) an acid of formula III:

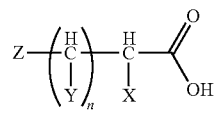

or a pharmaceutically acceptable salt, ester, or solvate thereof, wherein
    n is 0-6;
    X is H, OH, or $NH_2$,
    each Y is H or OH,
    or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;
    Z is H, $CH_3$, OH, COOH, or SH, provided that Y and Z are not both OH,
    or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N; and
    (e) mixtures thereof, wherein said composition maintains a concentration of degradation product(s) which is less than about 5% of the starting concentration of said active therapeutic agent.

In another preferred embodiment, the present inventive subject matter relates to a method for treating a disease, disorder, or condition in a mammal in need thereof, comprising administering to said mammal an effective amount of a foamable pharmaceutical composition, said composition comprising:

(i) an effective amount of one or more active therapeutic agents or pharmaceutically acceptable free bases, salts, esters, or solvates thereof;
(ii) a foamable delivery system which comprises:
  (a) a solvent composition selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof; and
  (b) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum derivative surfactant, an aliphatic amine surfactant, a polysiloxane derivative, a sorbitan fatty acid ester, pharmaceutically acceptable salts thereof, and mixtures thereof;
(iii) a propellant; and
(iv) an acid in an amount to affect the composition's pH selected from the group consisting of:
  (a) acetylsalicyclic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;

(b) an alpha hydroxyacid of formula I:

$(R_a)(R_b)C(OH)COOH$            I or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;

(c) an alpha ketoacid of formula II:

$(R_a)COCOO(R_b)$            II or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;

(d) an acid of formula III:

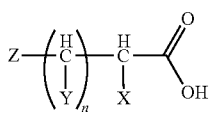

III or a pharmaceutically acceptable salt, ester, or solvate thereof, wherein n is 0-6;

X is H, OH, or $NH_2$, each Y is H or OH, or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;

Z is H, $CH_3$, OH, COOH, or SH, provided that Y and Z are not both OH, or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N; and (f) mixtures thereof.

In yet another preferred embodiment, the present inventive subject matter relates to a method for treating a skin condition in a mammal in need thereof, comprising administering to skin of said mammal an effective amount of a foamable pharmaceutical composition, said composition comprising:

(i) an effective amount of one or more active therapeutic agents or pharmaceutically acceptable free bases, salts, esters, or solvates thereof;

(ii) a foamable delivery system which comprises:

(a) a solvent composition selected from the group consisting of water, ethanol, isopropyl alcohol, benzyl alcohol, dimethyl isosorbide, propylene carbonate, xylene, methylene chloride, ethylhexanediol, polysiloxanes, dimethyl ether, and mixtures thereof; and (b) a surfactant composition selected from the group consisting of laureth-4, PEG-2 dilaurate, stearic acid, sodium lauryl sulfate, dioctyl sodium sulfosuccinate, cocoamphopropionate, poloxamer 188, meroxapol 258, triethanolamine, dimethicone, polysorbate 60, sorbitan monostearate, pharmaceutically acceptable salts thereof, and mixtures thereof;

(iii) a propellant; and (iv) an acid in an amount to affect the composition's pH selected from the group consisting of acetic acid, acetylsalicyclic acid, adipic acid, ascorbic acid, aspartic acid, benzoic acid, boric acid, carbonic acid, citric acid, formic acid, ethanesulfonic acid, fumaric acid, glycerophosphoric acid, gluconic acid, glutaric acid, glycine, glyceric acid, glycolic acid, glutamic acid, hippuric acid, hydrochloric acid, lactic acid, maleic acid, malic acid, malonic acid, mandelic acid, methanesulfonic acid, mucic acid, nitrous acid, oxalic acid, pelargonic acid, phosphoric acid, propionic acid, saccharin, salicylic acid, sorbic acid, succinic acid, sulfuric acid, tartaric acid, thioglycolic acid, thiosulfuric acid, undecylenic acid, ethanolamine, naturally and synthetically derived amino acids, derivatives thereof, and mixtures thereof.

In still yet another preferred embodiment, the present inventive subject matter relates to a method of making a foamable pharmaceutical composition, comprising the steps of:

(A) admixing an effective amount of one or more active therapeutic agents or pharmaceutically acceptable free bases, salts, esters, or solvates thereof and a pharmaceutically acceptable carrier comprising:

(i) a foamable delivery system which comprises:

(a) a solvent composition selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof; and (b) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum derivative surfactant, an aliphatic amine surfactant, a polysiloxane derivative, a sorbitan fatty acid ester, pharmaceutically acceptable salts thereof, and mixtures thereof; and (ii) an acid in an amount to affect the composition's pH selected from the group consisting of:

(a) acetylsalicyclic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;

(b) an alpha hydroxyacid of formula I:

$(R_a)(R_b)C(OH)COOH$            I or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;

(c) an alpha ketoacid of formula II:

$$(R_a)COCOO(R_b) \qquad \text{II}$$

or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;

(d) an acid of formula III:

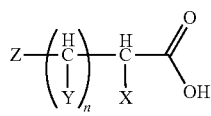

or a pharmaceutically acceptable salt, ester, or solvate thereof, wherein n is 0-6;

X is H, OH, or $NH_2$, each Y is H or OH, or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;

Z is H, $CH_3$, OH, COOH, or SH, provided that Y and Z are not both OH, or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N; and (e) mixtures thereof; and (B) packaging said mixture in a container suitable for storage and delivery of said composition.

In a further preferred embodiment, the present inventive subject matter relates to a method of delivering a foamable pharmaceutical composition from a container comprising providing an expelling force generated by mechanical means to said foamable pharmaceutical composition, said foamable pharmaceutical composition comprising:

(i) an effective amount of one or more active therapeutic agents or pharmaceutically acceptable free bases, salts, esters, or solvates thereof;

(ii) a foamable delivery system which comprises:
  (a) a solvent composition selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof; and
  (b) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum derivative surfactant, an aliphatic amine surfactant, a polysiloxane derivative, a sorbitan fatty acid ester, pharmaceutically acceptable salts thereof, and mixtures thereof; and (iii) an acid in an amount to affect the composition's pH selected from the group consisting of:
  (a) acetylsalicyclic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;
  (b) an alpha hydroxyacid of formula I:

$$(R_a)(R_b)C(OH)COOH \qquad \text{I}$$

or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;

(c) an alpha ketoacid of formula II:

$$(R_a)COCOO(R_b) \qquad \text{II}$$

or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;

(d) an acid of formula III:

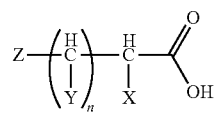

or a pharmaceutically acceptable salt, ester, or solvate thereof, wherein n is 0-6;

X is H, OH, or $NH_2$, each Y is H or OH, or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;

Z is H, $CH_3$, OH, COOH, or SH, provided that Y and Z are not both OH, or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N; and (e) mixtures thereof.

DETAILED DESCRIPTION OF THE INVENTION

DEFINITIONS

As used herein, an "aerosol" is a pressurized dosage form containing one or more active ingredients, and which upon actuation emits a dispersion of liquid and/or solid materials in a gaseous medium. The dosage form is packaged under pressure in a suitable container equipped with a valve assembly. When the valve is opened, the internal pressure forces the aerosol out the valve.

As used herein, "defoaming agent" or "foam inhibitor" refers to a solubilized surfactant, dispersion of hard particles, or dispersion of soft particles which interferes with foam formation or stability. Inhibition of foam production or stability may involve the addition of an insoluble liquid that is able to spread spontaneously, by virtue of surface-tension forces, over the surface of the foam films as they are formed. The spreading of the insoluble substance is so violent, and the spreading liquid drags along with it so much of the underlying film, that a hole is gouged in the film, which is thus destroyed. A liquid nonaqueous vehicle is generally present, even where the defoamer is represented as a solid formulation. A foam inhibitor typically provides a foam with quick-breaking attributes.

As used herein, "effecting" refers to the process of producing an effect on biological activity, function, health, or condition of an organism in which such activity is maintained, enhanced, diminished, or treated in a manner consistent with the general health and well-being of the organism.

As used herein, "enhancing" the biological activity, function, health, or condition of an organism refers to the process of augmenting, fortifying, strengthening, or improving.

As used herein, "epithelium" or "epithelial" refers to the layer of cells forming the epidermis of the skin and the surface layer of mucous and serous membranes. Epithelial cells have the general functions of protection, absorption, and secretion. Epithelial cells are often in close proximity to blood vessels, although generally lacking in a direct blood supply.

As used herein, "foam" refers to a coarse dispersion of gas in liquid in which the volume of the gas is considerably larger than that of the liquid. Accordingly, a foam is a tightly packed aggregation of gas bubbles, separated from each other by thin films of liquid (lamellae). The existence and stability of a foam depends on a surface layer of solute molecules. At the surface of a liquid, molecules are in a state of dynamic equilibrium, in which the net attractive forces exerted by the bulk of the fluid cause molecules to move out of the surface; this motion is counterbalanced by ordinary diffusion back into the diluted surface layer. The equilibrium results in the surface layer being constantly less dense than the bulk fluid, which creates a state of tension at the surface. The tension can be somewhat relieved by adsorption of foreign molecules either out of the bulk solution, or out of the vapor phase.

As used herein, "isomers" refer to different compounds that have the same molecular formula. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

As used herein, "pharmaceutically acceptable free bases, salts, esters, or solvates" refers to free bases, salts, esters, or solvates of subject compound(s) which possesses the same pharmacological activity as the subject compound(s) and which are neither biologically nor otherwise undesirable. A salt, ester, or solvate can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, ethanolamine, naturally and synthetically derived amino acids. Non-limiting examples of base salts, esters, or solvates include ammonium salts; alkali metal salts, such as sodium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others. Water or oil-soluble or dispersible products are thereby obtained.

As used herein, "propellant" refers to a substance that provides the pressure to an aerosol composition that forces the composition out of a container in which it is stored when a valve on the container is opened. Propellants also influence the form of the discharged composition, i.e. foam, stream, or spray. There are two common types of propellants, liquefied gases and compressed gases.

As used herein, "surface active agent" or "surfactant" refers to soluble substances that have a strong tendency to concentrate in the surface layer of a foam. Accordingly, a surface active agent will reduce interfacial surface tension at relatively low temperatures, making it easier for emulsification to take place. The addition of a surface active agent, then, will stabilize the foam by increasing the surface and bulk viscosities of the system, which reduces drainage, and by forming a strong interfacial film around the bubbles, retarding coalescence if the bubbles do come into contact.

Foamable Delivery Systems

The present inventive subject matter relates to a novel foamable delivery system which comprises:
(i) a solvent composition selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof;
(ii) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum derivative surfactant, an aliphatic amine surfactant, a polysiloxane derivative, a sorbitan fatty acid ester, pharmaceutically acceptable salts thereof, and mixtures thereof;

(iii) a propellant; and (iv) an acid in an amount to affect the delivery system's pH selected from the group consisting of:

(a) acetylsalicyclic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;

(b) an alpha hydroxyacid of formula I:

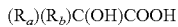    I or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;

(c) an alpha ketoacid of formula II:

    II or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;

(d) an acid of formula III:

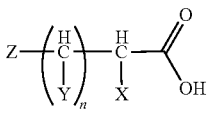    III or a pharmaceutically acceptable salt, ester, or solvate thereof, wherein n is 0-6;

X is H, OH, or $NH_2$, each Y is H or OH, or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;

Z is H, $CH_3$, OH, COOH, or SH, provided that Y and Z are not both OH, or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N; and (e) mixtures thereof.

The present inventive foamable delivery systems are capable of forming various kinds of foams for administration to epithelial cells of a mammal. For example, the present delivery systems may form dilute foams consisting of nearly spherical bubbles separated by rather thick films of somewhat viscous liquid. Similarly, the present delivery systems may form concentrated foams that are mostly gas phase and consist of polyhedral gas cells separated by thin liquid films. This concentrated foam may develop from the more dilute foam as a result of liquid drainage, or may develop directly from a liquid of relatively low viscosity.

Accordingly, the present inventive foam delivery systems promote foam stability by improving spreadability. Spreadability is a function of surface tension of the composition. An increase in surface tension is accompanied by an increase in surface area. Accordingly, it is expected that the present inventive compositions having one or more surfactants that produce a higher surface tension will improve the spreadability of the compositions. Such improved spreadability allows more intimate contact between the active therapeutic agent contained in the foam and the tissues to which foam is delivered.

The applied composition is initially in the form of a foam. The foam breaks down at physiological temperature to a liquid to allow the active therapeutic agent to saturate the treatment site. Such a system provides enhanced contact and penetration of the active therapeutic agent through the epithelial cell layer. Because the inventive composition is supplied as a foam, the properties of the composition make it easier to handle and physically control. The foamable composition disintegrates easily when spread and heated by the body, providing proper coverage at the site to be treated without premature evaporation of the solvent.

It would further be expected that the present foamable delivery systems maintain a concentration of degradation product(s) less than about 5% of the starting concentration of the active therapeutic agent contained therein, or less than 5% of the label claim, whichever is more stringent. In a preferred embodiment, the present inventive compositions can maintain a concentration of degradation product(s) less than about 2% of the starting concentration of the active agent. In this regard, it should be noted that these foamable delivery systems maintain a concentration of degradation product(s) less than the threshold limit for degradation product(s) established by the International Council on Harmonization of Technical Requirements for Registration of Pharmaceuticals for Human Use (ICH). Additionally, the label claim used to calculate the amount of the less than 10% degradation products of the label claim is intended to encompass that amount of active ingredient actually incorporated into the product to support this label claim, i.e. any amount remaining within the legal limits. Similar requirements for product stability for veterinary products are also herein envisioned.

In a preferred embodiment, the present inventive foamable delivery systems may optionally further comprise a foam inhibitor to aid in the spreading of the foam. Antifoaming agents (foam inhibitors) act against the various factors promoting foam stability. Accordingly, if rapid breakdown to a liquid state, as in a quick-breaking foam, and/or improved spreadability are desired, a foam inhibitor may be included in the present foam formulations.

Pharmaceutical Compositions

The present inventive subject matter additionally relates to a pharmaceutical composition comprising:
 (A) an effective amount of one or more active therapeutic agents or pharmaceutically acceptable free bases, salts, esters, or solvates thereof; and
 (B) a pharmaceutically acceptable carrier, comprising:
  (i) a foamable delivery system which comprises:
   (a) a solvent composition selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof; and
   (b) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum derivative surfactant, an aliphatic amine surfactant, a polysiloxane derivative, a sorbitan fatty acid ester, pharmaceutically acceptable salts thereof, and mixtures thereof;
  (ii) a propellant; and
  (iii) an acid in an amount to affect the composition's pH selected from the group consisting of:
   (a) acetylsalicylic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;
   (b) an alpha hydroxyacid of formula I:

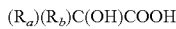
   $(R_a)(R_b)C(OH)COOH$     I or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;
   (c) an alpha ketoacid of formula II:

   $(R_a)COCOO(R_b)$     II or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;
   (d) an acid of formula III:

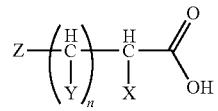

or a pharmaceutically acceptable salt, ester, or solvate thereof, wherein
   n is 0-6;
   X is H, OH, or $NH_2$,
   each Y is H or OH,
   or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;
   Z is H, $CH_3$, OH, COOH, or SH, provided that Y and Z are not both OH,
   or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N; and
   (e) mixtures thereof.

Active Agents

Examples of active therapeutic agents or their pharmaceutically acceptable free bases, salts, esters, or solvates useful in the present inventive compositions can be, but are not limited to, those selected from the group consisting of steroids, antifungal agents, antimicrobials, ureas and salts and derivatives thereof, cancer treating agents, treatment agents for inflammatory bowel disorders, agents intended to protect the skin, modify its appearance, or improve its rate of healing, and mixtures thereof.

In a preferred embodiment, said steroid is a corticosteroid that works to beneficially alter the appearance, metabolic or functional state, permeability, or health of a living organism. Corticosteroids are steroid hormones produced by the cortex of the adrenal gland. Preferred corticosteroids useful in the present inventive compositions include, but are not limited to, alclometasone dipropionate, amcinonide, beclamethasone dipropionate, betamethasone benzoate, betamethasone dipropionate, betamethasone valerate, budesonide, clobetasol propionate, clobetasone butyrate, cortisone acetate, desonide, desoximetasone, diflorasone diacetate, diflucortolone valerate, fluclorolone acetonide, flumethasone pivalate, fluocinolone acetonide, fluocinonide, fluocortin butyl, fluocortolone preparations, fluprednidene acetate, flurandrenolide, flurandrenolone, fluticasone propionate, halcinonide, halobetasol propionate, hydrocortisone, hydrocortisone acetate, hydrocortisone butyrate, hydrocortisone propionate, hydrocortisone valerate, methylprednisolone acetate, mometasone furoate, pramoxine hydrochloride, prednisone acetate, prednisone valerate, triamcinolone acetonide, and mixtures thereof.

In another preferred embodiment, said active therapeutic agent or its pharmaceutically acceptable free base, salt, ester, or solvate is an antifungal agent which can include, but is not limited to, those selected from the group consisting of imidazoles, hydroxy pyridones, triazoles, allyl amines, undecylenic acid derivatives, tolnaftate, haloprogin, pyridinethiones, cloquinol, and mixtures thereof.

Preferred antifungal agents useful in the present inventive compositions include, but are not limited to, amphotericin B, butoconazole nitrate, ciclopirox olamine, clindamycin, clioquinol, clotrimazole, econazole, econazole nitrate, fluconazole, flucytosine, griseofulvin, itraconazole, ketoconazole, miconazole, micronazole, naftifine, nystatin, omadine disulfide, sulconazole, terbinafine, terconazole, tioconazole, tolnaftate, triacetin, unecylenic acid, zinc pyrithione, and mixtures thereof.

In another preferred embodiment, said active therapeutic agent or its pharmaceutically acceptable free base, salt, ester, or solvate is an antimicrobial agent which can include, but is not limited to, those selected from the group consisting of amikacin, bacitracin, colistin, gentamicin, kanamycin, metronidazole, mupirocin, neomycin, netilmicin, polymyxin B, streptomycin, tobramycin, phenols and cresols such as 2,4-dichloro-sym-metaxylenol, parachlorometaxylenol, and parachlorometacresol, bisphenols such as hexachlorophene, dichlorophene, bithionol, triclosan, and fentichlor, salicylanilides such as 4',5-dibromsalicylanilide, 3',4',5-trichlorosalicylanilide, 3',4',5-tribromosalicylanilide, and 3,5,dibromo-3'-trifluoromethyl-salicylanilide, carbanilides such as trichlorocarbanilde and 3-trifluoromethyl-4-4'-dichlorocarbanilide, quaternary ammonium compounds such as alkyl-dimethyl benzyl ammonium chloride, alkyl-trimethyl ammonium chloride, alkyl trimethyl ammonium bromide, cetyl-trimethyl ammonium bromide, B-phenoxyethyl-dimethyl-dodecyl ammonium bromide, p-tert-octylphenoxyethoxyethyl-dimethyl-benzyl ammonium chloride, tetradecyl-pyridinium bromide, cetyl pyridinium bromide, cetyl pyridinium chloride, di-(n-octyl)-dimethyl ammonium bromide, alkyl-isoquinolinium bromide, 1-(3-chloroallyl)-3-5-7-triaza-1-azoniaadamantane chloride, and chlorhexidine (1,6,di(N-p-chlorophenylguanidino)hexane), 2-bromo-2-nitropropan-1,3-diol, imidazonidyl urea, ethanol, isopropyl alcohol, and mixtures thereof.

In another preferred embodiment, said active therapeutic agent or its pharmaceutically acceptable free base, salt, ester, or solvate is a skin-conditioning agent. Preferably, the skin-conditioning agent is selected from the group consisting of hydrocarbon oils and waxes, silicones, fatty acid derivatives, cholesterol, cholesterol derivatives, di- and tri-glycerides, vegetable oils, vegetable oil derivatives, liquid nondigestible oils such as those described in Mattson, U.S. Pat. No. 3,600,186, and Jandacek et al., U.S. Pat. Nos. 4,005,195 and 4,005,196, all of which are herein incorporated by reference in their entirety, or blends of liquid digestible or nondigestible oils with solid polyol polyesters such as those described in Jandacek, U.S. Pat. No. 4,797,300, and Letton, U.S. Pat. Nos. 5,306,514, 5,306,516, and 5,306,515, all of which are herein incorporated by reference in their entirety, acetoglyceride esters, alkyl esters, alkenyl esters, lanolin and its derivatives, milk tri-glycerides, wax esters, beeswax derivatives, sterols, phospholipids, and mixtures thereof.

In another preferred embodiment, said active therapeutic agent or its pharmaceutically acceptable free base, salt, ester, or solvate is an UV absorber/sunscreen agent. Preferably, the UV absorber/sunscreen agent is selected from the group consisting of p-aminobenzoic acid and its derivatives (ethyl, isobutyl, glycerly esters), p-dimethylaminobenzoic acid and its derivitatives (ethyl, isobutyl, glyceryl esters), o-aminobenzoates and its derivatives (methyl, menthyl, phenyl, benzyl, phenylethyl, linaly, terpenyl, and cyclohexenyl esters), salicylates (amyl, phenyl, benzyl, menthyl, glyceryl, and dipropylene-glycol esters), cinnamic acid derivatives (menthyl and benzyl esters; alphphenyl cinnamonitrile; butly cinnamoyl pyruvate, 2-ethylhexyl p-methoxycinnamate, iso-amyl p-methoxycinnamate), dihydroxycinnamic acid derivatives (umbelliferone, methyl-umbelliferone, methylaceto-umbelliferone), trihydroxycinnamic acid derivatives (esculetin, methylesculetin, daphnetin), hydrocarbons (diphenylbutadiene, stilbene), dibenzalacetone, benzalacetophenone, naphthosulphonates (sodium salts of 2-naphthol-3,6-disulphonic acid and of 2-naphthol-6,8-disulphonic acid), organic benzophenone derivatives (2,4-dihydroxybenzophenone, 2,2',4,4'-tetrahydroxybenzophenone, 2-hydroxy-4-methoxybenzophenone, 2-hydroxy-4-methoxybenzophenone-5-sulfonic acid, 2,2'-dihydroxy-4,4'-dimethoxybenzophenone, 2,2'-dihydroxy-4-methoxybenzophenone, disodium 2,2'-dihydroxy-4,4'-dimethoxy-5,5'-disulfobenzophenone), zinc oxide, titanium dioxide, and mixtures thereof.

In another preferred embodiment, said active therapeutic agent or its pharmaceutically acceptable free base, salt, ester, or solvate thereof is a urea or a salt or derivative thereof. In a particularly preferred embodiment, said active therapeutic agents or pharmaceutically acceptable free bases, salts, esters, or solvates thereof are a mixture of a urea or a salt or derivative thereof and an additional acceptable active therapeutic agent as set forth herein.

Other active therapeutic agents commonly known as useful in the preparation of topical pharmaceutical compositions are further contemplated as within the scope of the present inventive subject matter.

Solvents

One of the major uses of the solvents included in the present compositions is to bring the active therapeutic agent into solution with the propellant. It is often necessary to use a solvent to obtain a homogenous mixture of these components. The solvents also help produce a spray with the desired particle size and help reduce the vapor pressure of the propellant.

Examples of solvents useful in the present inventive compositions can be, but are not limited to, those selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof.

Preferred volatile propellants useful as solvents in the present inventive compositions include, but are not limited to, hydrocarbon propellants such as propane, isopropane, n-butane, and isobutene, chlorofluorocarbons (CFCs), hydrofluoroalkanes (HFAs), and dimethyl ether.

In a particularly preferred embodiment, said solvent composition is selected from the group consisting of water, ethanol, isopropyl alcohol, benzyl alcohol, dimethyl isosorbide, propylene carbonate, xylene, methylene chloride, ethylhexanediol, polysiloxanes, dimethyl ether, and mixtures thereof.

Other solvents commonly known as useful in the preparation of foamable compositions are further contemplated as within the scope of the present inventive subject matter.

Surfactants

Most aerosol foam products are formulated with water-soluble or water-dispersible surface active agents. Accordingly, the aerosol products will foam when discharged unless significant quantities of a foam depressant are present.

A wide variety of surfactants can be employed in the foam delivery systems of the present inventive compositions. These surfactants can include, for example, polyoxyethylene fatty ethers, polyoxyethylene fatty esters, fatty acids, sulfated fatty acids, phosphated fatty acids, sulfosuccinates, amphoteric surfactants, non-ionic poloxamers, non-ionic meroxapols, petroleum derivatives, aliphatic amines, polysiloxane derivatives, sorbitan fatty acid esters, pharmaceutically acceptable salts thereof, and mixtures thereof.

In a preferred embodiment, the surfactant is a polyoxyethylene fatty ether. Particular polyoxyethylene fatty ethers useful in the present inventive compositions can include those of the formula:

$$CH_3(CH_2)_xCH_2(OCH_2CH_2)_nOH,$$

wherein n is 4-8 and x is 6-20, and pharmaceutically acceptable salts thereof. Laureth-4 and pharmaceutically acceptable salts thereof are particularly preferred in this regard. Other specific polyoxyethylene fatty ethers useful in the present inventive compositions include laureth-9, undeceth-9, ceteth-1, ceteareth-2, steareth-1, steareth-2, steareth-21, PEG-2 stearate, PEG-6 stearate, PEG-8 dilaurate, pharmaceutically acceptable salts thereof, and mixtures thereof.

In another preferred embodiment, the surfactant is a polyoxyethylene fatty ester. Particular polyoxyethylene fatty esters useful in the present inventive compositions can include those of the formula:

$$H_3C(CH_2)_xC(O)(OCH_2CH_2)_nOC(O)(CH_2)_yCH_3,$$

wherein n is 2-90, x is 6-20, and y is 6-20, and pharmaceutically acceptable salts thereof. PEG-2 dilaurate and pharmaceutically acceptable salts thereof are particularly preferred in this regard. Other specific polyoxyethylene fatty esters useful in the present inventive compositions include PEG-150 laurate, PEG-150 distearate, PEG-78 glyceryl cocoate, PEG-30 glyceryl cocoate, ceteth-1, ceteth-2, ceteth-6, ceteth-10, ceteth-12, ceteareth-2, ceteareth-6, ceteareth-10, ceteareth-12, steareth-1, steareth-2, steareth-6, steareth-10, steareth-12, PEG-2 stearate, PEG-4 stearate, PEG-6 stearate, PEG-10 stearate, PEG-12 stearate, PEG-20 glyceryl stearate, PEG-80 glyceryl tallowate, PPG-10 glyceryl stearate, PEG-80 glyceryl cocoate, PEG-200 glyceryl tallowate, PEG-8 dilaurate, PEG-10 distearate, pharmaceutically acceptable salts thereof, and mixtures thereof.

In another preferred embodiment, the surfactant is a fatty acid. Particular fatty acids useful in the present inventive compositions can include lauric acid, myristic acid, palmitic acid, stearic acid, arachidic acid, oleic acid, linoleic acid, linolenic acid, eleostearic acid, arachidonic acid, isostearic acid, hydroxystearic acid, ricinoleic acid, behenic acid, erucic acid, lanolin acid, pharmaceutically acceptable salts thereof, and mixtures thereof. Stearic acid is particularly preferred in this regard.

In another preferred embodiment, the surfactant is a sulfated fatty acid surfactant. Particular sulfated fatty acid surfactants useful in the present inventive compositions can include those of the formula:

$$H_3C(CH_2)_nCH_2OSO_3X,$$

wherein n is 10-22 and X is H, Li, Na, or K, and pharmaceutically acceptable salts thereof. Sodium lauryl sulfate and other pharmaceutically acceptable salts thereof are particularly preferred in this regard. Other specific sulfated fatty acid surfactants useful in the present inventive compositions include sodium laureth(3)sulfate, ammonium lauryl sulfate, ammonium laureth(3)sulfate, potassium lauryl sulfate, potassium laureth(3)sulfate, TEA lauryl sulfate, TEA laureth(3) sulfate, pharmaceutically acceptable salts thereof, and mixtures thereof.

In another preferred embodiment, the surfactant is a phosphated fatty acid surfactant. Particular phosphated fatty acid surfactants useful in the present inventive compositions can include those of the formula:

$$H_3C(CH_2)_nCH_2OPO_3X,$$

wherein n is 10-22 and X is Be, Mg, or Ca, and pharmaceutically acceptable salts thereof.

In another preferred embodiment, the surfactant is a sulfosuccinate surfactant. Particular sulfosuccinate surfactants useful in the present inventive compositions can include those of the formula:

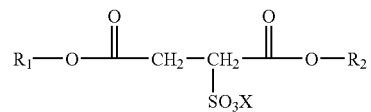

wherein $R_1$ and $R_2$ are each independently a $C_1$-$C_9$ straight or branched chain alkyl, a $C_2$-$C_9$ straight or branched chain alkenyl, or a $C_2$-$C_9$ straight or branched chain alkynyl; and X is H, Li, Na, or K, and pharmaceutically acceptable salts thereof. Dioctyl sodium sulfosuccinate, or diethylhexyl sodium sulfosuccinate, and pharmaceutically acceptable salts thereof are particularly preferred in this regard. Other specific sulfosuccinate surfactants useful in the present inventive compositions include sodium bis(2-ethylhexyl)sulfosuccinate, disodium N-octadecylsulfosuccinnate, disodium lauryl sulfosuccinate, diammonium lauryl sulfosuccinate, tetrasodium N-(1,2-dicarboxyethyl)-N-octadecylsulfosuccinnate, sodium dioctyl sulfosuccinate, disodium oleamido MEA sulfosuccinate, pharmaceutically acceptable salts thereof, and mixtures thereof.

In another preferred embodiment, the surfactant is an amphoteric surfactant. Particular amphoteric surfactants useful in the present inventive compositions include those of the formula:

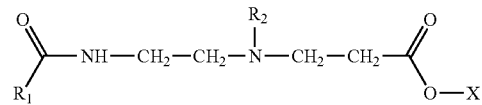

wherein $R_1$ is a fatty acid;

$R_2$ is a $C_1$-$C_9$ straight or branched chain alkyl alcohol, a $C_2$-$C_9$ straight or branched chain alkenyl alcohol, or a $C_2$-$C_9$ straight or branched chain alkynyl alcohol; and X is H, Li, Na, or K, and pharmaceutically acceptable salts thereof. Cocoamphopropionate is particularly preferred in this regard. In particular, the sodium cocoamphopropionate salt is particularly preferred. Other specific amphoteric surfactants useful in the present inventive compositions include cocoamphocarboxypropionic acid, cocoamphocarboxypropionate, cocoamphoglycinate, cocoamphocarboxyglycinate, cocoamphoacetate, cocoamphodiacetate, cocoamphodipropionate, alkyl glycinates, propionates, imidazolines, amphoalkylsulfonates, N-alkylaminopropionic acids, N-alkyliminodipropionic acids, imidazoline carboxylates, N-alkylbetaines, amido propyl betaines, sarcosinates, amine oxides, sulfobetaines, sultaines, lauramphocarboxyglycinate, lauramphopropionate, stearampho-glycinate, tallowamphopropionate, tallowamphoglycinate, oleoamphoglycinate, caproamphoglycinate, caprylamphopropionate, caprylamphocarboxyglycinate, cocoyl imidazoline, lauryl imidazoline, stearyl imidazoline, behenyl imidazoline, behenylhydroxyethyl imidazoline, caprylamphopropylsulfonate, cocamphopropylsulfonate, stearamphopropyl-sulfonate, oleoampho-propylsulfonate, pharmaceutically acceptable salts thereof, and mixtures thereof.

In another preferred embodiment, the surfactant is a non-ionic poloxamer surfactant. Particular non-ionic poloxamer surfactants useful in the present inventive compositions include those of the formula:

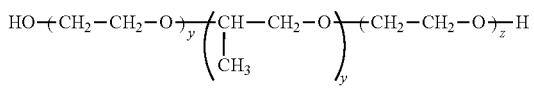

wherein
x is 8-75;
y is 30-35; and
z is 8-75, and pharmaceutically acceptable salts thereof. Poloxamer 188 and pharmaceutically acceptable salts thereof are particularly preferred in this regard. Other specific non-ionic poloxamer surfactants useful in the present inventive compositions include Poloxamer 124, Poloxamer 237, Poloxamer 338, Poloxamer 407, Pluronic, Supronic, Synperonic, Monolan, Lutrol, pharmaceutically acceptable salts thereof, and mixtures thereof.

In another preferred embodiment, the surfactant is a non-ionic meroxapol surfactant. Particular non-ionic meroxapol surfactants useful in the present inventive compositions can include those of the formula:

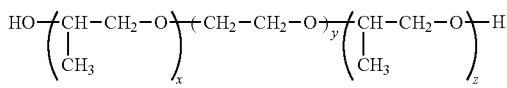

wherein
x is 18-21;
y is 7-163; and
z is 18-21, and pharmaceutically acceptable salts thereof. Meroxapol 258 and pharmaceutically acceptable salts thereof are particularly preferred in this regard. Other specific meroxapol surfactants useful in the present inventive compositions include Meroxapol 105, Meroxapol 108, Meroxapol 171, Meroxapol 172, Meroxapol 174, Meroxapol 178, Meroxapol 251, Meroxapol 252, Meroxapol 254, Meroxapol 255, Meroxapol 311, Meroxapol 312, and Meroxapol 314, pharmaceutically acceptable salts thereof, and mixtures thereof.

In another preferred embodiment, the surfactant is a petroleum derivative surfactant. Particular petroleum derivative surfactants useful in the present inventive compositions include those selected from the group consisting of mineral oil, microcrystalline wax, and distillates.

In another preferred embodiment, the surfactant is an aliphatic amine surfactant. Particular aliphatic amine surfactants useful in the present inventive compositions include those of the formula:

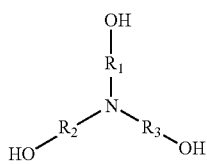

wherein
$R_1$, $R_2$, and $R_3$ are each independently a $C_1$-$C_9$ straight or branched chain alkyl, and pharmaceutically acceptable salts thereof. Triethanolamine and pharmaceutically acceptable salts thereof are particularly preferred in this regard. Other specific aliphatic amine surfactants useful in the present inventive compositions include triisopropanolamine, trimethanolamine, tributanolamine, propanol-diethanolamine, pharmaceutically acceptable salts thereof, and mixtures thereof.

In another preferred embodiment, the surfactant is a polysiloxane derivative. Particular polysiloxane derivatives useful in the present inventive compositions include those of the formula:

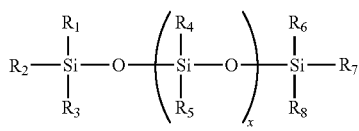

wherein
x is 2-500; and
$R_1$, $R_2$, $R_3$, $R_4$, $R_5$, $R_6$, $R_7$, and $R_8$ are each independently H, $C_1$-$C_{22}$ straight or branched chain alkyl, $C_2$-$C_{22}$ straight or branched chain alkenyl, $C_2$-$C_{22}$ straight or branched chain alkynyl, $C_1$-$C_{22}$ straight or branched chain alkoxy, $C_6$-$C_{14}$ aryl, $C_6$-$C_{22}$ alkyl-substituted aryl, or $C_6$-$C_{22}$ aryl substituted aryl, and pharmaceutically acceptable salts thereof. Dimethicone and pharmaceutically acceptable salts thereof are particularly preferred in this regard. Other specific polysiloxanes useful in the present inventive compositions include poly(dimethylsiloxane) (PDMS), cyclomethicone, hexomethyl methicone, polymethyl-hydrosiloxane (PMHS), cyclotetra(methylhydrosiloxane) (D4H), diethylpolysiloxane, high molecular weight dimethicone, mixed $C_1$-$C_{30}$ alkyl polysiloxane, phenyl dimethicone, dimethiconol, pharmaceutically acceptable salts thereof, and mixtures thereof. One of ordinary skill in the art would appreciate that each of said polysiloxanes or polysiloxane derivatives can be used either as a solvent or as a surfactant.

In another preferred embodiment, the surfactant is a sorbitan fatty acid ester. Particular sorbitan fatty acid esters useful in the present inventive compositions include polysorbate 60, sorbitan monostearate, and pharmaceutically acceptable salts thereof. Other specific sorbitan fatty acid esters useful in the present inventive compositions include sorbitan laurate, sorbitan oleate, sorbitan palmitate, sorbitan stearate, sorbitan trioleate, sorbitan sesquioleate, sorbitan monoisosteareate, sorbitan sesqui-isostearate, sorbitan trilaurate, sorbitan tristearate, sorbitan di-isostearate, sorbitan dioleate, sorbitan sesquistearate, sorbitan tri-isostearate, polysorbate 20, polysorbate 21, polysorbate 40, polysorbate 61, polysorbate 65, polysorbate 80, polysorbate 81, polysorbate 85, polysorbate 120, pharmaceutically acceptable salts thereof, and mixtures thereof.

In a particularly preferred embodiment, said surfactant composition is selected from the group consisting of laureth-4, PEG-2 dilaurate, stearic acid, sodium lauryl sulfate, dioctyl sodium sulfosuccinate, cocoamphopropionate, poloxamer 188, meroxapol 258, triethanolamine, dimethicone, polysorbate 60, sorbitan monostearate, pharmaceutically acceptable salts thereof, and mixtures thereof.

Other surfactants commonly known as useful in the preparation of foamable compositions are further contemplated as within the scope of the present inventive subject matter. These other surfactants include, for example, those listed in the *CTFA Cosmetic Ingredient Dictionary*, Second Edition, The Cosmetic Toiletry and Fragrance Association, Inc., 1133 Fifteenth Street, N.W., Washington, D.C. 20005, 1977, the entire contents of which are hereby incorporated by reference.

Propellants

When the propellant is a liquefied gas or a mixture of liquefied gases, it frequently serves the dual role of propellant and solvent or vehicle for the product concentrate. As the propellant meets the air, it may immediately evaporate due to the drop in pressure, leaving the product concentrate as airborne liquid droplets or dry particles, or it may remain with the product droplets as a solvent for the product.

The propellants employed in the present inventive compositions can include, for example, those selected from the classes of hydrocarbons (e.g. propane, isobutane, n-butane, and mixtures thereof) or petroleum gases, chlorofluorocarbons (CFC's), hydrofluoroalkanes (HFA's), dimethyl ether, propane-isobutane, non-soluble compressed gasses (e.g. air, oxygen, hydrogen, and nitrogen), soluble compressed gasses (e.g. carbon dioxide and nitrous oxide), methylene chloride, and mixtures thereof. In a preferred embodiment, said propellant is a volatile propellant that is dimethyl ether.

Other propellants commonly known as useful in the preparation of foamable compositions are further contemplated as within the scope of the present inventive subject matter.

When used in aerosols, compressed gases, in comparison to liquefied gases, have the advantages that they are odorless, colorless, low in toxicity, nonflammable, inexpensive, more pressure stable, and environmentally acceptable. These advantages need to be balanced against the compressed gas disadvantages, which include inferior spray characteristics, changes in spray characteristics during discharge, increased potential for loss of the gas, valve and actuator clogging, and increased potential for corrosion, in selecting the propellant for use in the present aerosols.

Acids

The acids useful in the present inventive compositions encompass those that have the desired effect on the pH of the compositions. In particular, the acids used ensure that the present inventive compositions maintain a suitable pH of about 2 to about 10. A wide variety of acids are suitably effective. These acids can include, for example, ascorbic acid, alpha hydroxyacids, alpha ketoacids, other organic or inorganic acids, pharmaceutically acceptable salts thereof, and mixtures thereof.

In a preferred embodiment, the acid is an alpha hydroxyacid of the formula I:

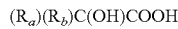

or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH, or alkoxy group having 1 to 9 carbon atoms.

Exemplary alpha hydroxyacids useful in the present inventive compositions include, but are not limited to, agaricic acid, allonic acid, alpha hydroxylauric acid, alpha hydroxymyristic acid, alpha hydroxypalmitic acid, alpha hydroxystearic acid, alpha hydroxyarachidonic acid, altronic acid, arabinoic acid, atrolactic acid, benzilic acid, citramalic acid, citric acid, isocitric acid, erythronic acid, galactonic acid, galactoheptonic acid, galacturonic acid, gluconic acid, glucoheptonic acid, glucuronic acid, glyceric acid, glycolic acid, gulonic acid, 2-hydroxybutanoic acid, 2-hydroxypentanoic acid, 2-hydroxyhexanoic acid, 2-hydroxyheptanoic acid, 2-hydroxyactanoic acid, 2-hydroxynonanoic acid, 2-hydroxydecanoic acid, 2-hydroxyundecanoic acid, idonic acid, lactic acid, methyllactic acid, phenyllactic acid, 3-(2'-hydroxyphenyl)lactic acid, 3-(4'-hydroxyphenyl)lactic acid, lyxonic acid, malic acid, mandelic acid, 4-chloromandelic acid, 4-hydroxymandelic acid, 3,4-dihydroxymandelic acid, 3-hydroxy-4-methoxymandelic acid, 4-hydroxy-3-methoxymandelic acid, mannoic acid, mucic acid, ribonic acid, saccharic acid, talonic acid, tartaric acid, tartronic acid, thioglycolic acid, threonic acid, xylonic acid, and pharmaceutically acceptable salts thereof.

In a further preferred embodiment, the acid is an alpha ketoacid of the formula II:

or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms.

Exemplary alpha ketoacids useful in the present inventive compositions include, but are not limited to, benzoylformic acid, methyl benzoyl formate, ethyl benzoyl formate, glyoxylic acid, methyl 2-ketoethanoate, 2-ketobutanoic acid, 2-ketopentanoic acid, 2-ketohexanoic acid, 2-ketoheptanoic acid, 2-ketooctanoic acid, methyl 2-ketooctanoate, 2-ketodecanoic acid, pyruvic acid, methyl pyruvate, ethyl pyruvate, propyl pyruvate, phenylpyruvic acid, methyl phenylpyruvate, ethyl phenylpyruvate, and pharmaceutically acceptable salts thereof.

In another preferred embodiment, the acid is an acid of formula III:

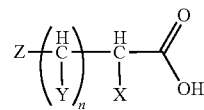

or a pharmaceutically acceptable salt, ester, or solvate thereof, wherein n is 0-6;

X is H, OH, or $NH_2$, each Y is H or OH, or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;

Z is H, $CH_3$, NH, $NH_2$, OH, COOH, or SH, provided that Y and Z are not both OH, or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N. It is to be noted in this regard that where the acid of formula III contains an $NH_2$ group or nitrogen containing heterocyclic ring, this acid behaves as an amphoteric or pseudoamphoteric substance. It is additionally contemplated that the carboxylic acid group on the acid of formula III can be replaced with a phosphoric, phosphonic, sulfonic, sulfinic, or sulfate group.

Exemplary acids of the formula III useful in the present inventive compositions include, but are not limited to, acetic acid, adipic acid, alanine, asparagine, aspartic acid, benzoic acid, cysteine, cystine, glutamic acid, glutamine, glutaric acid, glycine, glycylglycine, histidine, glycylhistidine, leucine, isoleucine, lysine, 5-hydroxylysine, malonic acid, pelargonic acid, phenylalanine, proline, 3-hydroxyproline, 4-hydroxyproline, propionic acid, salicylic acid, serine, succinic acid, threonine, tryptophan, tyrosine, valine, and pharmaceutically acceptable salts thereof.

Other amphoteric or pseudoamphoteric compounds may additionally be used in the present inventive compositions to have the desired effect on the pH of the compositions. These other compounds can include, but are not limited to, homocysteine, homocystine, homoserine, ornithine, citrulline, creatine, 3-aminopropanoic acid, theanine, 2-aminobutanoic acid, 4-aminobutanoic acid, ethanolamine, 2-amino-2-methylpropanoic acid, 2-methyl-3-aminopropanoic acid, 2,6-diaminopimelic acid, 2-amino-3-phenylbutanoic acid, phenylglycine, canavanine, canaline, 4-hydroxyarginine, 4-hydroxyornithine, homoarginine, 4-hydroxyhomoarginine, β-lysine, 2,4-diaminobutanoic acid, 2,3-diaminopropanoic acid, 2-methylserine, 3-phenylserine, betaine, arginine, histidine, taurine, cysteine sulfinic acid, glycylhistidine, cocoamphoglycine, cocoamphopropionate, cocoamphopropylsulphonate, phosphatidyl ethanolamine, phosphatidyl serine, sphingomyelin, stearamidoethyl diethylamine, stearamidoethyl diethanolamine, stearamidopropyl dimethylamine, and pharmaceutically acceptable salts thereof.

Further exemplary additional acids useful in the present inventive compositions to have the desired effect on the pH of the compositions include, but are not limited to, quinic acid, isocitric acid, tropic acid, trethocanic acid, 3-chloractic acid, cerebronic acid, citramalic acid, agaricic acid, 2-hydroxynervonic acid, aleuritic acid, acetylsalicylic acid, boric acid, carbonic acid, formic acid, ethanesulfonic acid, fumaric acid, glycerophosphoric acid, hippuric acid, hydrochloric acid, maleic acid, methanesulfonic acid, nitrous acid, phosphoric acid, sorbic acid, sulfuric acid, thiosulfuric acid, undecylenic acid, pantoic acid, and pharmaceutically acceptable salts thereof.

Each of these acids may be present in the present inventive compositions in a free acid, lactone, or ester form, or in a salt form with an organic base or an inorganic alkali.

In a particularly preferred embodiment, said acid useful in the present inventive compositions is selected from the group consisting of acetic acid, acetylsalicylic acid, adipic acid, ascorbic acid, aspartic acid, benzoic acid, boric acid, carbonic acid, citric acid, formic acid, ethanesulfonic acid, fumaric acid, glycerophosphoric acid, gluconic acid, glutaric acid, glycine, glyceric acid, glycolic acid, glutamic acid, hippuric acid, hydrochloric acid, lactic acid, maleic acid, malic acid, malonic acid, mandelic acid, methanesulfonic acid, mucic acid, nitrous acid, oxalic acid, pelargonic acid, phosphoric acid, propionic acid, saccharin, salicylic acid, sorbic acid, succinic acid, sulfuric acid, tartaric acid, thioglycolic acid, thiosulfuric acid, undecylenic acid, ethanolamine, naturally and synthetically derived amino acids, derivatives thereof, and mixtures thereof.

Other acids commonly known as useful in the preparation of foamable compositions are further contemplated as within the scope of the present inventive subject matter.

The acid included in the present inventive compositions is selected to maintain a suitable pH of the composition of about 2 to about 10. The optimal pH of the composition, and the acid and amount of same used to maintain this optimal pH, will vary depending on the particular active therapeutic agent contained in the composition. This optimal pH for each specific active agent, as well as the selection of the optimal type and quantity of acid to achieve this optimal pH, are contemplated as within the scope of knowledge generally available to those of ordinary skill in the art.

Additional Ingredients

In addition to the active therapeutic agent and the foamable delivery system, the pharmaceutical preparations of the invention may additionally comprise other nonessential, optional ingredients known to a person of ordinary skill in the art as suitable for a topical foam. For example, the instant pharmaceutical preparations may optionally further include one or more preservatives well known in the art, such as benzoic acid, sorbic acid, methylparaben, propylparaben, ethylenediaminetetraacetic acid (EDTA), benzyl alcohol, phenoxyethanol, DMDM hydantoin, and imidazolidinyl urea. These preservatives may be present in amounts up to about 1% and preferably from about 0.05 to about 0.5% by weight of the pharmaceutical composition. Other additional optional ingredients may include thickeners and viscosity modifiers such as diethanolamide of a long chain fatty acid, fatty alcohols (i.e. cetearyl alcohol), sodium chloride, sodium sulfate, ethyl alcohol, hydroxyethyl cellulose, and Carbomer; coloring agents such as any of the FD&C or D&C dyes; hair oxidizing (bleaching) agents such as hydrogen peroxide, perborate salts, and persulfate salts; hair reducing agents such as the thioglycolates; perfumes; moisturizers, emollients; plasticizers; stabilizers; skin penetrating agents; and chelating agents such as disodium EDTA The present inventive pharmaceutical compositions may also be packaged in a container suitable for storage and delivery of said composition.

Methods of Treatment

The present inventive subject matter further relates to a method for treating a disease, disorder, or condition in a mammal in need thereof, comprising administering to said mammal an effective amount of a foamable pharmaceutical composition, said composition comprising:

(i) an effective amount of one or more active therapeutic agents or pharmaceutically acceptable free bases, salts, esters, or solvates thereof;

(ii) a foamable delivery system which comprises:

(a) a solvent composition selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof; and (b) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum derivative surfactant, an aliphatic amine surfactant, a polysiloxane derivative, a sorbitan fatty acid ester, pharmaceutically acceptable salts thereof, and mixtures thereof;

(iii) a propellant; and (iv) an acid in an amount to affect the composition's pH selected from the group consisting of:
  (a) acetylsalicyclic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;
  (b) an alpha hydroxyacid of formula I:

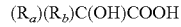    I or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;
  (c) an alpha ketoacid of formula II:

    II or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;
  (d) an acid of formula III:

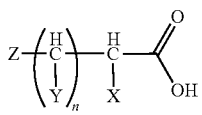    III or a pharmaceutically acceptable salt, ester, or solvate thereof, wherein
  n is 0-6;
  X is H, OH, or $NH_2$,
  each Y is H or OH,
  or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;
  Z is H, $CH_3$, OH, COOH, or SH, provided that Y and Z are not both OH,
  or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N; and
  (e) mixtures thereof.

The present pharmaceutical compositions and foamable delivery systems can be used to treat a wide variety of dermatological diseases, disorders, or conditions in a mammal, especially diseases affecting mammalian tissue. Examples of such diseases include, but are not limited to, eczema, infantile eczema, psoriasis, scalp psoriasis, atopic dermatitis, dermatitis herpetiformis, contact dermatitis, seborrheic dermatitis, neurodermatitis, pruritis, fungal diseases, and intertrigo.

For example, if corticosteroids, particularly ester compounds, are used in the present inventive compositions, these compositions are effective in the treatment of skin diseases such as eczema, infantile eczema, atopic dermatitis, dermatitis herpetiformis, contact dermatitis, seborrheic dermatitis, neurodermatitis, psoriasis, pruritis, and intertrigo in humans.

Similarly, if antifungal agents are used in the present inventive compositions, these compositions are effective in the treatment of fungal diseases, including dermatophyte infections such as tinea corporis, tinea pedis, tinea unguium, tinea capitis, tinea cruris, and tinea barbae; and yeast infections such as candidiasis and tinea versicolor. Other fungal diseases are further contemplated as within the scope of the present inventive subject matter.

In a particularly preferred embodiment, the disease treated by the present inventive composition is eczema.

The treatment of other dermatological diseases known in the art as effectively treated with a topical composition is further contemplated as within the scope of the present inventive subject matter.

In another preferred embodiment, said foamable pharmaceutical composition is administered topically to mucosal epithelial cell tissues of the mouth, ear, nasal passages, vagina, urethra, or rectum. Although the target of oral and nasal tissues may be such tissues themselves, oral and nasal preparations may also be absorbed and produce systemic effects.

In certain instances and for local effects, drugs are inserted into the vagina, urethra, or rectum. Systemic drug effects may also result after the vaginal, urethral, or rectal application of drugs due to absorption of the drug from the mucous membranes of these sites. Aerosol foams can be used intravaginally in essentially the same manner as that employed for creams. The aerosol package contains an inserter device filled with foam. The inserter device is contents placed in the vagina where the contents thereof are released through activation of a plunger. Similarly, preparations of urethral or rectal foams use inserters for the presentation of the foam into the urethral or anal canal, respectively.

Methods of Production

The present inventive subject matter further relates to a method of making a foamable pharmaceutical composition, comprising the steps of:
  (A) admixing an effective amount of one or more active therapeutic agents or pharmaceutically acceptable free bases, salts, esters, or solvates thereof and a pharmaceutically acceptable carrier comprising:
    (i) a foamable delivery system which comprises:
      (a) a solvent composition selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof; and
      (b) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum derivative surfactant, an aliphatic amine surfactant, a polysiloxane derivative, a sorbitan fatty acid ester, pharmaceutically acceptable salts thereof, and mixtures thereof; and (ii) an acid in an amount to affect the composition's pH selected from the group consisting of:

(a) acetylsalicyclic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;

(b) an alpha hydroxyacid of formula I:

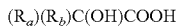

$(R_a)(R_b)C(OH)COOH$  I or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;

(c) an alpha ketoacid of formula II:

$(R_a)COCOO(R_b)$  I or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;

(d) an acid of formula III:

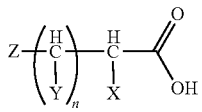

or a pharmaceutically acceptable salt, ester, or solvate thereof, wherein
n is 0-6;
X is H, OH, or $NH_2$,
each Y is H or OH,
or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;
Z is H, $CH_3$, OH, COOH, or SH, provided that Y and Z are not both OH,
or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N; and
(e) mixtures thereof; and (B) packaging said mixture in a container suitable for storage and delivery of said composition.

The compositions made according to this method are preferably in an aerosol dosage form suitable for topical application. Accordingly, said production method can additionally comprise the further step of charging the container with a propellant suitable to effect aerosol delivery of the composition from the container.

The effectiveness of the present pharmaceutical aerosol formulations depends on achieving the proper combination of formulation, container, and valve assembly.

The Container

The instant foamable pharmaceutical compositions are preferably packaged in a container as an aerosol. The compositions may be packaged in the container using either a single-step or a multiple-step filling process commonly known to those of ordinary skill in the art.

The container must be selected to provide the aerosol formulation with a long shelf life. Accordingly, the container must be chemically inert with respect to the composition contained therein so as not to interfere with the stability of the formulation or with the integrity and operation of the container. Further, the container must be capable of withstanding the pressure required by the product, must be corrosive-resistant, and must be resistant to physical or chemical changes to the product contained therein that may, for example, form particles clogging the orifice. This is particularly important as the present compositions contain a surfactant and an acid, two components known to increase the potential for corrosion.

The selection of a suitable container for the aerosol product is based on its adaptability to production methods, compatibility with formulation components, ability to sustain the pressure intended for the product, the interest in design and aesthetic appeal on the part of the manufacturer, and cost. Suitable containers may be made of, for example, steel, aluminum, glass, plastic, or mixtures thereof. The containers may further employ one or more protective coatings such as, for example, sodium nitrate, sodium benzoate, ammonium m-nitrobenzoate, morpholine, 2-methyl butynoyl, Expoxol 9-5, sodium n-lauroylsarcosinate, phenolic, epoxy, or vinyl coatings, to enhance the formulation compatibility or safe handling. Any other known aerosol containers and protective coatings are further contemplated as useful in this regard.

The container may also comprise two or more compartments permitting the final composition to be broken up into separate portions that are physically separated until dispensed from the container through the valve assembly.

Known methods for filling aerosol containers with foamable compositions include processes known as cold fill, under the cup, and pressure fill (through the valve). Such methods for filling an aerosol container are well known to those of ordinary skill in the art and may be found in *The Aerosol Handbook* (Wayne E. Dorland, Caldwell, N.J.) and *the Handbook of Aerosol Technology*, (R. E. Krieger, Malabar, Fla.), both of which are incorporated by reference in their entirety.

In the cold filling method, both the product concentrate and the propellant must be cooled to temperatures of −30° to −40° F. The chilled product concentrate is quantitatively metered into an equally cold aerosol container, then the cold, liquefied gas is added. When sufficient propellant has been added, the valve assembly is placed on the container.

In the under the cap filling method, a filling head that forms a tight seal on the container shoulder is utilized. The filling head holds the valve above the container while propellant under pressure is added through the opening in the container.

In the pressure filling method, the product concentrate is quantitatively placed in the container, the valve assembly is placed on the container, and the liquefied gas, under pressure, is metered through the valve stem into the container. Pressure filling is used for most pharmaceutical aerosols.

Valve Assembly

The function of the valve assembly is to permit the expulsion of the contents of the can in the desired form, at the desired rate, and, in the case of metered valves, in the proper amount or dose. Accordingly, the valve assembly must contribute to the form of the product to be emitted. In particular, aerosol foam valves typically have a large-diameter delivery spout to permit the delivery of the foam. Further, the valve assembly permits the aerosol composition to be released from the container either via continuous delivery or as a metered dose.

The materials used in the manufacture of the valve assembly must be inert towards the aerosol formulations that pass therethrough. Among the materials that can be used in the manufacture of the various valve parts are plastic, rubber, aluminum, stainless steel, and mixtures thereof. The usual aerosol valve assembly is composed of the following parts: actuator, stem, gasket, spring, mounting cup, housing, and dip tube. Valves may also be employed that permit emission of product while the container is upright or inverted. All types of valve assemblies known to those of ordinary skill in the art, including spray valves, sliding gasket valves, deflecting gasket valves, and tilt action valves, are contemplated as capable of delivering the present inventive compositions.

Metering valves are designed to deliver specific quantities of a product each time the valve is actuated. Meter valves are usually employed when the formulation is a potent medication or in other instances where a precise dosing is desired. In metered valve systems, an auxiliary valve chamber regulates the amount of material discharged by virtue of its capacity or dimensions.

The valve assembly may further accommodate an attachment to facilitate delivery of the present inventive foamable pharmaceutical compositions.

Methods of Delivery

The present inventive subject matter further relates to a method of delivering a foamable pharmaceutical composition from a container comprising providing an expelling force generated by mechanical means to said foamable pharmaceutical composition, said foamable pharmaceutical composition comprising:

(i) an effective amount of one or more active therapeutic agents or pharmaceutically acceptable free bases, salts, esters, or solvates thereof;

(ii) a foamable delivery system which comprises:
  (a) a solvent composition selected from the group consisting of water, a volatile propellant, a $C_1$-$C_6$ fluid alkyl or branched alkyl alcohol, an aromatic alcohol, an ether of a sorbitol derivative, propylene carbonate, xylene, methylene chloride, ethylhexanediol, polysiloxanes, dimethyl ether, and mixtures thereof; and
  (b) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum derivative surfactant, an aliphatic amine surfactant, a polysiloxane derivative, a sorbitan fatty acid ester, pharmaceutically acceptable salts thereof, and mixtures thereof; and (iii) an acid in an amount to affect the composition's pH selected from the group consisting of:
  (a) acetylsalicyclic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;
  (b) an alpha hydroxyacid of formula I:

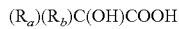

$(R_a)(R_b)C(OH)COOH$    I or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;
  (c) an alpha ketoacid of formula II:

$(R_a)COCOO(R_b)$    II or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;
  (d) an acid of formula III:

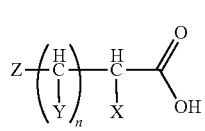

III or a pharmaceutically acceptable salt, ester, or solvate thereof, wherein
  n is 0-6;
  X is H, OH, or $NH_2$,
  each Y is H or OH,
  or X and Y are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N;
  Z is H, $CH_3$, OH, COOH, or SH, provided that Y and Z are not both OH,
  or Y and Z are optionally taken together to form a 5-7 membered saturated or unsaturated carbocyclic ring or a 5-7 membered saturated or unsaturated heterocyclic ring, wherein one or more ring atom(s) of said heterocyclic ring is O, S, or N; and
  (e) mixtures thereof.

The expelling force used to deliver the composition from a container can take the form of pressure applied to the aerosol system through the use of one or more liquefied or gaseous propellants. Alternatively, the composition may be expelled from the container through the use of a compressed gas generated by mechanical means, such as by a pump action or a squeezing action on the container. Other expelling forces known to those of ordinary skill in the art are further contemplates as within the scope of the present inventive subject matter.

Upon activation of the valve assembly, it is the pressure exerted by the propellant which forces the contents of the package out through the opening of the valve. This expelling force allows the present inventive compositions to be delivered as a fine mist; a coarse, wet or a dry spray; a steady stream; or as a stable or breaking foam. The contemplated foams include those intended for deposition on the skin or for instillation into a body cavity, such as vaginal foams, urethral foams, oral and aural foams, and rectal foams.

The pressure of an aerosol is critical to its performance. It can be controlled by 1) the type and amount of propellant and 2) the nature and amount of material comprising the product concentrate. Thus, each formulation is unique, and a specific amount of propellant to be employed in aerosol products is determined by the skilled practitioner. In general, foam aerosols usually operate between about 10 to about 200 psig at 70° F., preferably between about 13 and about 108 psig at 70° F. and more preferably between about 20 and about 80 psig at 70° F. Further, foam aerosols may contain about 1 to about 90% propellant, preferably from about 2 to about 50% propellant, and more preferably between about 2.5 and about 20% propellant.

Advantages to Aerosol Delivery Systems

When formulated as pharmaceutical aerosol foams, the present inventive compositions exhibit several properties that may be considered advantages over other types of dosage forms. These include:

1. A portion of medication may be easily withdrawn from the package without contamination or exposure to the remaining material.

2. By virtue of its hermetic character, the aerosol container protects medicinal agents adversely affected by atmospheric oxygen and moisture. Being opaque, the usual aerosol containers also protect drugs adversely affected by light. This protection persists during the use and the shelf-life of the product. If the product is packaged under sterile conditions, sterility may also be maintained during the shelf-life of the product.

3. Topical medication may be applied in a uniform, thin layer to epithelial cell tissues, without touching the affected area. This method of application may reduce the irritation that sometimes accompanies the mechanical (fingertip) application of topical preparations. The rapid volatilization of the propellant also provides a cooling, refreshing effect.

4. By proper formulation and valve control, the physical form and the particle size of the emitted product may be controlled, contributing to the efficacy of the drug. For example, a transdermal drug is expected to have greater efficacy when maintained in contact with epithelial cell tissues for a longer period of time and when transported in a vehicle which enhances absorption.

5. Aerosol application is a "clean" process, requiring little or no "wash-up" by the user.

6. Through the use of metered valves, dosage may be controlled.

Dosage

Appropriate dosage levels for the active therapeutic agents contemplated in the present inventive subject matter are well known to those of ordinary skill in the art. Dosage levels on the order of about 0.001 mg to about 5,000 mg per kilogram body weight of the active therapeutic compounds or compositions are known to be useful in the treatment of the diseases, disorders, and conditions contemplated in the present invention. Typically, this effective amount of the active therapeutic agents will generally comprise from about 0.1 mg to about 100 mg per kilogram of patient body weight per day. Moreover, it will be understood that this dosage of active therapeutic agents can be administered in a single or multiple dosage units to provide the desired therapeutic effect. If desired, other therapeutic agents can be employed in conjunction with those provided by the present inventive subject matter.

The present inventive compositions may be given in a single or multiple doses daily. In a preferred embodiment, the present inventive compositions are given from one to three times daily. Starting with a low dose twice daily and slowly working up to higher doses if needed is a preferred strategy. The amount of active ingredients that may be combined with the carrier materials to produce a single dosage form will vary depending upon the host treated, the nature of the disease, disorder, or condition, and the nature of the active ingredients.

It is understood, however, that a specific dose level for any particular patient will depend upon a variety of factors well known in the art, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

The optimal pharmaceutical formulations will be determined by one skilled in the art depending upon considerations such as the particular drug or drug combination and the desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the therapeutic agents.

EXAMPLES

The following examples are illustrative of the present inventive subject matter and are not intended to be limitations thereon. Unless otherwise indicated, all percentages are based upon 100% by weight of the final composition.

Example 1

The following example illustrates the preparation of a foamable pharmaceutical composition of the present inventive subject matter:

|  | % W/W |
| --- | --- |
| Clobetasol Propionate | 0.05 |
| Poloxamer 188 | 1.60 |
| Citric Acid Buffer | 0.15 |
| Ethyl Alcohol | 60.0 |
| Polysorbate 60 | 0.10 |
| Propylene Glycol | 2.00 |
| Purified Water | 31.6 |
| Propellant (Propane-Isobutane) | 4.50 |
|  | 100.0% |

Preparation of the Composition:

1. Combine the materials, exclusive of the propellant, by conventional means to form an aerosol concentrate.

2. The concentrate is then filled into an aerosol container, such as an aluminum tube.

3. The propellant is then added via conventional procedures, such as by through-the-valve or under-the-cup methods of charging.

Example 2

The following example illustrates the preparation of a foamable pharmaceutical composition of the present inventive subject matter:

|  | % W/W |
|---|---|
| Betamethasone Valerate | 0.10 |
| Laureth-4 | 3.00 |
| Phosphoric Acid Buffer | 0.20 |
| Ethyl Alcohol | 65.0 |
| Diethylhexyl sodium sulfosuccinate | 1.00 |
| Glycerin | 3.00 |
| Purified Water | 23.4 |
| Propellant (Propane-Isobutane) | 4.30 |
|  | 100.0% |

Preparation of the Composition:

1. Combine the materials, exclusive of the propellant, by conventional means to form an aerosol concentrate.
2. The concentrate is then filled into an aerosol container, such as an aluminum tube.
3. The propellant is then added via conventional procedures, such as by through-the-valve or under-the-cup methods of charging.

Example 3

The following example illustrates the preparation of a foamable pharmaceutical composition of the present inventive subject matter:

|  | % W/W |
|---|---|
| Ciclopirox Olamine | 2.00 |
| Isopropyl Alcohol | 45.0 |
| Benzyl Alcohol | 1.00 |
| Sorbic Acid Buffer | 1.00 |
| Dimethicone | 1.00 |
| Sodium Cocoamphopropionate | 3.50 |
| Sodium Lauryl Sulfate | 0.50 |
| Dimethyl Ether | 2.00 |
| Purified Water | 41.0 |
| Propellant (propane-isobutane) | 3.00 |
|  | 100.0% |

Preparation of the Composition:

1. Combine the materials, exclusive of the propellant, by conventional means to form an aerosol concentrate.
2. The concentrate is then filled into an aerosol container, such as an aluminum tube.
3. The propellant is then added via conventional procedures, such as by through-the-valve or under-the-cup methods of charging.

Example 4

The following example illustrates the preparation of a foamable pharmaceutical composition of the present inventive subject matter:

|  | % W/W |
|---|---|
| Clindamycin Phosphate | 2.40 |
| Propylene Glycol | 5.00 |
| Phosphoric Acid Buffer | 0.30 |
| Ethyl Alcohol | 25.0 |
| Isopropyl Alcohol | 25.0 |
| Dimethyl Isosorbide | 1.00 |
| PEG-2 Dilaurate | 4.00 |
| Triethanolamine | q.s. to pH ~4.5 |
| Propellant (Propane-Isobutane) | 6.00 |
| Purified Water | Balance |
|  | 100.0% |

Preparation of the Composition:

1. Combine the materials, exclusive of the propellant, by conventional means to form an aerosol concentrate.
2. The concentrate is then filled into an aerosol container, such as an aluminum tube.
3. The propellant is then added via conventional procedures, such as by through-the-valve or under-the-cup methods of charging.

Example 5

The following example illustrates a generally applicable method for the preparation of a composition of the present inventive subject matter:

Preparation of a foamable pharmaceutical composition is accomplished by conventional means. The materials, exclusive of the propellant, are combined to form an aerosol concentrate. If the artisan preparing the composition so chooses, smaller groups of ingredients may be combined first, to form two or more phases which are later combined into the final aerosol concentrate. Preparation of multiple phases is particularly useful when, for example, a subset of ingredients is preferably combined when heated or cooled to a temperature above or below ambient, combined at sub- or super-atmospheric pressure, or combined under a specialized atmosphere, such as pure nitrogen or oxygen.

The concentrate is then filled into an aerosol container, such as an aluminum tube, and the propellant added via conventional procedures, such as through-the-valve or under-the-cup methods of charging. The finished aerosol dispensing system additionally employs a suitable valve and applicator nozzle that permit the medicament to be administered in close proximity to the area to be treated, externally or within a body cavity.

Example 6

The following example illustrates a generally applicable method for administering a composition of the present inventive subject matter:

A foamable pharmaceutical composition is administered topically to the skin of the patient being treated by conventional means. This is preferably done through the use of an aerosol package. Such aerosol packages designed for topical delivery to epithelial cell tissues are convenient and often result in higher patient compliance. A topical preparation may thus be applied to the desired surface area with or without the use of the fingertips, making the procedure less messy than with most other types of topical preparations.

For topical administration of aerosol dosage forms, the patient should be told to first clean the affected area gently and to pat it dry. Product may then be applied directly to the affected area or dispensed into the palm of the hand or suitable vessel from which material may be taken and manually applied to the area to be treated. The patient should allow the product applied to dry and not cover the area with a bandage or dressing unless instructed to do so by the physician. The patient should avoid accidentally instilling or bringing the product into contact with the eyes or mouth.

Example 7

A patient is suffering from psoriasis. A foamable pharmaceutical composition of the present inventive subject matter, comprising a corticosteroid as the active therapeutic agent, is topically administered to the patient. It would be expected that the patient would improve his/her condition or recover. In addition, it would also be expected that the inventive composition would provide improved delivery of the corticosteroid, decreased inconvenience and irritation, increased ease of use for the patient, and reduced degradation of the corticosteroid during storage of the product.

Example 8

A patient is suffering from tinea pedis. A foamable pharmaceutical composition of the present inventive subject matter, comprising an antifungal agent as the active therapeutic agent, is topically administered to the patient. It would be expected that the patient would improve his/her condition or recover. In addition, it would also be expected that the inventive composition would provide improved delivery of the antifungal agent, decreased inconvenience and irritation, increased ease of use for the patient, and reduced degradation of the antifungal agent during storage of the product.

Example 9

A patient is suffering from eczema. A foamable pharmaceutical composition of the present inventive subject matter, comprising an antifungal agent as the active therapeutic agent, is topically administered to the patient. It would be expected that the patient would improve his/her condition or recover. In addition, it would also be expected that the inventive composition would provide improved delivery of the antifungal agent, decreased inconvenience and irritation, increased ease of use for the patient, and reduced degradation of the antifungal agent during storage of the product.

Example 10

A patient is suffering from infantile eczema. A foamable pharmaceutical composition of the present inventive subject matter, comprising an antifungal agent as the active therapeutic agent, is topically administered to the patient. It would be expected that the patient would improve his/her condition or recover. In addition, it would also be expected that the inventive composition would provide improved delivery of the antifungal agent, decreased inconvenience and irritation, increased ease of use for the patient, and reduced degradation of the antifungal agent during storage of the product.

Example 11

A patient is suffering from atopic dermatitis. A foamable pharmaceutical composition of the present inventive subject matter, comprising an antifungal agent as the active therapeutic agent, is topically administered to the patient. It would be expected that the patient would improve his/her condition or recover. In addition, it would also be expected that the inventive composition would provide improved delivery of the antifungal agent, decreased inconvenience and irritation, increased ease of use for the patient, and reduced degradation of the antifungal agent during storage of the product.

Example 12

A patient is suffering from dermatitis herpetiformis. A foamable pharmaceutical composition of the present inventive subject matter, comprising an antifungal agent as the active therapeutic agent, is topically administered to the patient. It would be expected that the patient would improve his/her condition or recover. In addition, it would also be expected that the inventive composition would provide improved delivery of the antifungal agent, decreased inconvenience and irritation, increased ease of use for the patient, and reduced degradation of the antifungal agent during storage of the product.

Example 13

A patient is suffering from contact dermatitis. A foamable pharmaceutical composition of the present inventive subject matter, comprising an antifungal agent as the active therapeutic agent, is topically administered to the patient. It would be expected that the patient would improve his/her condition or recover. In addition, it would also be expected that the inventive composition would provide improved delivery of the antifungal agent, decreased inconvenience and irritation, increased ease of use for the patient, and reduced degradation of the antifungal agent during storage of the product.

Example 14

A patient is suffering from seborrheic dermatitis. A foamable pharmaceutical composition of the present inventive subject matter, comprising an antifungal agent as the active therapeutic agent, is topically administered to the patient. It would be expected that the patient would improve his/her condition or recover. In addition, it would also be expected that the inventive composition would provide improved delivery of the antifungal agent, decreased inconvenience and irritation, increased ease of use for the patient, and reduced degradation of the antifungal agent during storage of the product.

Example 15

A patient is suffering from neurodermatitis. A foamable pharmaceutical composition of the present inventive subject matter, comprising an antifungal agent as the active therapeutic agent, is topically administered to the patient. It would be expected that the patient would improve his/her condition or recover. In addition, it would also be expected that the inventive composition would provide improved delivery of the antifungal agent, decreased inconvenience and irritation, increased ease of use for the patient, and reduced degradation of the antifungal agent during storage of the product.

Example 16

A patient is suffering from pruritis. A foamable pharmaceutical composition of the present inventive subject matter, comprising an antifungal agent as the active therapeutic agent, is topically administered to the patient. It would be expected that the patient would improve his/her condition or recover. In addition, it would also be expected that the inventive composition would provide improved delivery of the antifungal agent, decreased inconvenience and irritation, increased ease of use for the patient, and reduced degradation of the antifungal agent during storage of the product.

Example 17

A patient is suffering from intertrigo. A foamable pharmaceutical composition of the present inventive subject matter, comprising an antifungal agent as the active therapeutic agent, is topically administered to the patient. It would be expected that the patient would improve his/her condition or recover. In addition, it would also be expected that the inventive composition would provide improved delivery of the antifungal agent, decreased inconvenience and irritation, increased ease of use for the patient, and reduced degradation of the antifungal agent during storage of the product.

The inventive subject matter being thus described, it will be apparent that the same may be modified or varied in many ways. Such modifications and variations are not to be regarded as a departure from the spirit and scope of the inventive subject matter, and all such modifications and variations are intended to be included within the scope of the following claims.

We claim:

1. A method of delivering a foamable pharmaceutical composition from a container comprising providing an expelling force generated by mechanical means selected from the group consisting of a pump action and a squeezing action to said foamable pharmaceutical composition, said foamable pharmaceutical composition comprising:
    (i) an effective amount of one or more active therapeutic agents or pharmaceutically acceptable free bases, salts, esters, or solvates thereof;
    (ii) a foamable delivery system which comprises:
        (a) a solvent composition selected from the group consisting of water, a $C_1$-$C_6$ fluid alkyl or branched alkyl alcohol, an aromatic alcohol, an ether of a sorbitol, propylene carbonate, xylene, methylene chloride, ethylhexanediol, polysiloxanes, dimethyl ether, and mixtures thereof; and
        (b) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum surfactant, an aliphatic amine surfactant, a polysiloxane, a sorbitan fatty acid ester, pharmaceutically acceptable salts thereof, and mixtures thereof; and
    (iii) an acid in an amount to affect the composition's pH selected from the group consisting of:
        (a) acetylsalicylic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;
        (b) an alpha hydroxyacid of formula I:

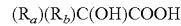

$$(R_a)(R_b)C(OH)COOH \qquad \text{I}$$

or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ are unsubstituted or are substituted with an OH, SH, CHO, COOH group;
        (c) an alpha ketoacid of formula II:

$$(R_a)COCOO(R_b) \qquad \text{II}$$

or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ is unsubstituted or is substituted with an F, Cl, Br, I, OH, CHO, COOH, or alkoxy group having 1 to 9 carbon atoms;
        (d) an acid of formula III:

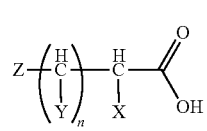

III or a pharmaceutically acceptable salt, ester, or solvate thereof, wherein
        n is 0-6;
        X is H, OH, or $NH_2$,
        each Y is H or OH,
        or Y and Z can be taken together to form a 5-7 membered saturated or unsaturated carbocyclic ring or a 5-7 membered saturated or unsaturated heterocyclic ring, wherein one or more ring atom(s) of said heterocyclic ring is O, S, or N;
        Z is H, $CH_3$, OH, COOH, or SH, provided that Y and Z are not both OH, or Y and Z can be taken together to form a 5-7 membered saturated or unsaturated carbocyclic ring or a 5-7 membered saturated or unsaturated heterocyclic ring, wherein one or more ring atom(s) of said heterocyclic ring is O, S, or N; and
        (e) mixtures thereof;
wherein said foamable delivery system does not include a fatty alcohol.

2. The method of claim 1, wherein said expelling force is created by a pump action.

3. The method of claim 1, wherein said expelling force is generated by a squeezing action.

4. The method of claim 1, wherein the pharmaceutical composition is effective for treating a disease, disorder, or condition in a mammal in need thereof when applied to epithelial cell tissues of said mammal.

5. The method of claim 1, wherein said one or more active therapeutic agents or pharmaceutically acceptable free bases, salts, esters, or solvates thereof are selected from the group consisting of steroids, antifungal agents, antimicrobials, ureas and salts thereof, cancer treating agents, treatment agents for inflammatory bowel disorders, agents intended to protect the skin, modify its appearance, or improve its rate of healing, and mixtures thereof.

6. The method of claim 5, wherein said steroid is a corticosteroid which is selected from the group consisting of alclometasone dipropionate, amcinonide, beclamethasone dipropionate, betamethasone benzoate, betamethasone dipropionate, betamethasone valerate, budesonide, clobetasol propionate, clobetasone butyrate, cortisone acetate, desonide, desoximetasone, diflorasone diacetate, diflucortolone valerate, fluclorolone acetonide, flumethasone pivalate, fluocinolone acetonide, fluocinonide, fluocortin butyl, fluocortolone preparations, fluprednidene acetate, flurandrenolide, flurandrenolone, fluticosone propionate, halcinonide, halobetasol propionate, hydrocortisone, hydrocortisone acetate, hydrocortisone butyrate, hydrocortisone propionate, hydrocortisone valerate, methylprednisolone acetate, mometasone furoate, pramoxine hydrochloride, prednisone acetate, prednisone valerate, triamcinolone acetonide, and mixtures thereof.

7. The method of claim 5, wherein said antifungal agent is selected from the group consisting of imidazoles, hydroxy pyridones, triazoles, allyl amines, undecylenic acids, tolnaftate, haloprogin, pyridinethiones, cloquinol, and mixtures thereof.

8. The method of claim 5, wherein said antifungal agent is selected from the group consisting of amphotericin B, butoconazole nitrate, ciclopirox olamine, clindamycin, clioquinol, clotrimazole, econazole, econazole nitrate, fluconazole, flucytosine, griseofulvin, itraconazole, ketoconazole, miconazole, micronazole, naftifine, nystatin, omadine disulfide, sulconazole, terbinafine, terconazole, tioconazole, tolnaftate, triacetin, unecylenic acid, zinc pyrithione, and mixtures thereof.

9. The method of claim 1, wherein said one or more active therapeutic agents or phamiaceutically acceptable free bases, salts, esters, or solvates thereof comprise a urea or a salt thereof either alone or in combination with an additional active therapeutic agent.

10. The method of claim 1, wherein said composition has a concentration of degradation product(s) less than about 5% of the starting concentration of said active therapeutic agent or its pharmaceutically acceptable salt, ester, or solvate.

11. The method of claim 10, wherein said composition has a concentration of degradation product(s) less than about 2% of the starting concentration of said active therapeutic agent or its pharmaceutically acceptable salt, ester, or solvate.

12. The method of claim 1, wherein said solvent composition is selected from the group consisting of water, ethanol, isopropyl alcohol, benzyl alcohol, dimethyl isosorbide, propylene carbonate, xylene, methylene chloride, ethylhexanediol, polysiloxanes, dimethyl ether, and mixtures thereof.

13. The method of claim 1, wherein said surfactant composition is selected from the group consisting of:

(a) a compound of the formula:

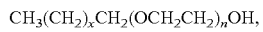

wherein n is 4-8 and x is 6-20;

(b) a compound of the formula:

H$_3$C(CH$_2$)$_x$C(O)(OCH$_2$CH$_2$)$_n$OC(O)(CH$_2$)$_y$CH$_3$, wherein n is 2-90, x is 6-20, and y is 6-20;

(c) a compound of the formula:

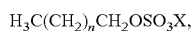

wherein n is 10-22 and X is H, Li, Na, or K;

(d) a compound of the formula:

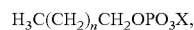

wherein n is 10-22 and X is Be, Mg, or Ca;

(e) a compound of the formula:

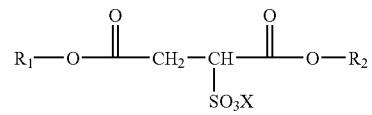

wherein

R$_1$ and R$_2$ is each independently a C$_1$-C$_9$ straight or branched chain alkyl, a C$_2$-C$_9$ straight or branched chain alkenyl, or a C$_2$-C$_9$ straight or branched chain alkynyl; and X is H, Li, Na, or K;

(f) a compound of the formula:

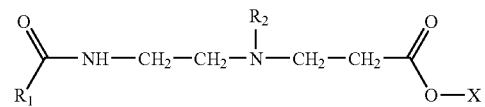

wherein

R$_1$ is a fatty acid;

R$_2$ is a C$_1$-C$_9$ straight or branched chain alkyl alcohol, a C$_2$-C$_9$ straight or branched chain alkenyl alcohol, or a C$_2$-C$_9$ straight or branched chain alkynyl alcohol; and X is H, Li, Na, or K;

(g) a compound of the formula:

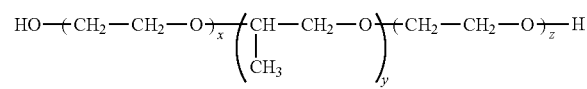

wherein x is 8-75;

y is 30-35; and z is 8-75;

(h) a compound of the formula:

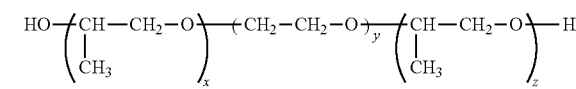

wherein x is 18-21;

y is 7-163; and z is 18-21;

(i) mineral oil, microcrystalline wax, and distillates;

(j) a compound of the formula:

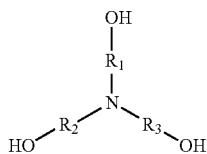

wherein
R$_1$, R$_2$, and R$_3$ are each independently a C$_1$-C$_9$ straight or branched chain alkyl;
(k) a compound of the formula:

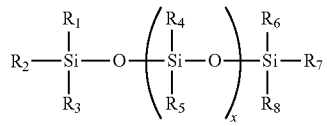

wherein
x is 2-500; and
R$_1$, R$_2$, R$_3$, R$_4$, R$_5$, R$_6$, R$_7$, and R$_8$ are each independently H, C$_1$-C$_{22}$ straight or branched chain alkyl, C$_2$-C$_{22}$ straight or branched chain alkenyl, C$_2$-C$_{22}$ straight or branched chain alkynyl, C$_1$-C$_{22}$ straight or branched chain alkoxy, C$_6$-C$_{14}$ aryl, C$_6$-C$_{22}$ alkyl-substituted aryl, or C$_6$-C$_{22}$ aryl substituted aryl;
(l) polysorbate 60 and sorbitan monostearate;
(m) pharmaceutically acceptable salts thereof; and
(n) mixtures thereof.

14. The method of claim 13, wherein said surfactant composition is selected from the group consisting of laureth-4, PEG-2 dilaurate, stearic acid, sodium lauryl sulfate, dioctyl sodium sulfosuccinate, cocoamphopropionate, poloxamer 188, meroxapol 258, triethanolamine, dimethicone, polysorbate 60, sorbitan monostearate, pharmaceutically acceptable salts thereof, and mixtures thereof.

15. The method of claim 1, wherein said acid is selected from the group consisting of acetic acid, acetylsalicylic acid, adipic acid, ascorbic acid, aspartic acid, benzoic acid, boric acid, carbonic acid, citric acid, formic acid, ethanesulfonic acid, fumaric acid, glycerophosphoric acid, gluconic acid, glutaric acid, glycine, glyceric acid, glycolic acid, glutamic acid, hippuric acid, hydrochloric acid, lactic acid, maleic acid, malic acid, malonic acid, mandelic acid, methanesulfonic acid, mucic acid, nitrous acid, oxalic acid, pelargonic acid, phosphoric acid, propionic acid, saccharin, salicylic acid, sorbic acid, succinic acid, sulfuric acid, tartaric acid, thioglycolic acid, thiosulfuric acid, undecylenic acid, ethanolamine, and mixtures thereof.

16. The method of claim 1, wherein said composition additionally comprises a foam inhibitor.

17. The method of claim 1, wherein said composition is packaged in a container suitable for storage and delivery of said composition.

18. The method of claim 17, wherein said container is composed of steel, aluminum, glass, plastic, or mixtures thereof.

19. The method of claim 17, wherein said container further comprises one or more protective coatings.

20. The method of claim 17, wherein said container comprises two or more compartments permitting the composition to be physically separated into two separate portions until dispensed from the container through a valve assembly.

21. A method of delivering a pharmaceutical composition from a container comprising providing an expelling force generated by mechanical means selected from the group consisting of a pump action and a squeezing action to said pharmaceutical composition, said pharmaceutical composition comprising:
(A) an effective amount of one or more active therapeutic agents or pharmaceutically acceptable free bases, salts, esters, or solvates thereof; and
(B) a pharmaceutically acceptable carrier, comprising:
(i) a foamable delivery system which comprises:
(a) a solvent composition selected from the group consisting of water, ethanol, isopropyl alcohol, benzyl alcohol, dimethyl isosorbide, propylene carbonate, xylene, methylene chloride, ethylhexanediol, polysiloxanes, dimethyl ether, and mixtures thereof; and
(b) a surfactant composition selected from the group consisting of laureth-4, PEG-2 dilaurate, stearic acid, sodium lauryl sulfate, dioctyl sodium sulfosuccinate, cocoamphopropionate, poloxamer 188, meroxapol 258, triethanolamine, dimethicone, polysorbate 60, sorbitan monostearate, pharmaceutically acceptable salts thereof, and mixtures thereof; and
(ii) an acid in an amount to affect the composition's pH selected from the group consisting of acetic acid, acetylsalicylic acid, adipic acid, ascorbic acid, aspartic acid, benzoic acid, boric acid, carbonic acid, citric acid, founic acid, ethanesulfonic acid, fumaric acid, glycerophosphoric acid, gluconic acid, glutaric acid, glycine, glyceric acid, glycolic acid, glutamic acid, hippuric acid, hydrochloric acid, lactic acid, maleic acid, malic acid, malonic acid, mandelic acid, methanesulfonic acid, mucic acid, nitrous acid, oxalic acid, pelargonic acid, phosphoric acid, propionic acid, saccharin, salicylic acid, sorbic acid, succinic acid, sulfuric acid, tartaric acid, thioglycolic acid, thiosulfuric acid, undecylenic acid, ethanolamine, naturally and synthetically derived amino acids, and mixtures thereof
wherein said foamable delivery system does not include a fatty alcohol.

22. A method of delivering a pharmaceutical composition from a container comprising providing an expelling force generated by mechanical means selected from the group consisting of a pump action and a squeezing action to said pharmaceutical composition, said pharmaceutical composition comprising a starting concentration of an active therapeutic agent comprising:
(A) an effective amount of one or more active therapeutic agents or pharmaceutically acceptable free bases, salts, esters, or solvates thereof; and
(B) a pharmaceutically acceptable carrier, comprising:
(i) foamable delivery system which comprises:
(a) a solvent composition selected from the group consisting of water, a C$_1$-C$_6$ fluid alkyl or branched alkyl alcohol, an aromatic alcohol, an ether of a sorbitol, propylene carbonate, xylene, methylene chloride, ethylhexanediol, polysiloxanes, dimethyl ether, and mixtures thereof; and
(b) a surfactant composition selected from the group consisting of a polyoxyethylene fatty ether, a polyoxyethylene fatty ester, a fatty acid, a sulfated fatty acid surfactant, a phosphated fatty acid surfactant, a sulfosuccinate surfactant, an amphoteric surfactant, a non-ionic poloxamer surfactant, a non-ionic meroxapol surfactant, a petroleum surfactant, an aliphatic amine surfactant, a polysiloxane, a sorbitan fatty acid ester, pharmaceutically acceptable salts thereof, and mixtures thereof; and (ii) an acid in an amount to affect the composition's pH selected from the group consisting of:

(a) acetylsalicyclic acid, ascorbic acid, boric acid, carbonic acid, formic acid, ethanesulfonic acid, fumaric acid, glycerophosphoric acid, hippuric acid, hydrochloric acid, maleic acid, methanesulfonic acid, nitrous acid, oxalic acid, phosphoric acid, saccharin, sorbic acid, sulfuric acid, thiosulfuric acid, undecylenic acid, ethanolamine, and a pharmaceutically acceptable salt, ester, or solvate thereof;

(b) an alpha hydroxyacid of formula I:

$$(R_a)(R_b)C(OH)COOH \qquad I$$

or a pharmaceutically acceptable salt, lactone, or solvate thereof wherein $R_a$ and $R_b$ are independently selected from the group consisting of H, F, Cl, Br, and saturated or unsaturated, isomeric or non-isomeric, straight, branched, or cyclic $C_i$-$C_{25}$ alkyl, aralkyl, or aryl groups, wherein each of $R_a$ and $R_b$ are unsubstituted or are substituted with an OH, SH, CHO, COOH group;

(c) an alpha ketoacid of formula II:

$$(R_a)COCOO(R_b) \qquad II$$

or a pharmaceutically acceptable salt, ester, or solvate thereof wherein $R_a$ and $R_b$ are independently selected from the group consisting of H and saturated or unsaturated, isomeric or non-isomeric, straight, branched, or cyclic $C_i$-$C_{25}$ alkyl, aralkyl, or aryl groups, wherein $R_a$ is unsubstituted or is substituted with an F, Cl, Br, I, OH, CHO, COOH, or alkoxy group having 1 to 9 carbon atoms;

(d) an acid of formula III:

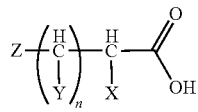

or a pharmaceutically acceptable salt, ester, or solvate thereof, wherein n is 0-6;

X is H, OH, or $NH_2$, each Y is H or OH, or X and Y can be taken together to form a 5-7 membered saturated or unsaturated carbocyclic ring or a 5-7 membered saturated or unsaturated heterocyclic ring, wherein one or more ring atom(s) of said heterocyclic ring is O, S, or N;

Z is H, $CH_3$, OH, COOH, or SH, provided that Y and Z are not both OH, or Y and Z can be taken together to form a 5-7 membered saturated or unsaturated carbocyclic ring or a 5-7 membered saturated or unsaturated heterocyclic ring, wherein one or more ring atom(s) of said heterocyclic ring is O, S, or N; and (e) mixtures thereof, wherein said composition maintains a concentration of degradation product(s) less than about 5% of the starting concentration of said active therapeutic agent or its pharmaceutically acceptable salt, ester, or solvate;

wherein said foamable delivery system does not include a fatty alcohol.

23. The method of claim 22, wherein said composition has a concentration of degradation product(s) less than about 2% of the starting concentration of said active therapeutic agent or its pharmaceutically acceptable salt, ester, or solvate.

* * * * *

UNITED STATES PATENT AND TRADEMARK OFFICE
CERTIFICATE OF CORRECTION

PATENT NO. : 7,829,107 B2  
APPLICATION NO. : 11/595864  
DATED : November 9, 2010  
INVENTOR(S) : Karl F. Popp and Edward R. Yuhas Page 1 of 1

It is certified that error appears in the above-identified patent and that said Letters Patent is hereby corrected as shown below:

Claim 1, Column 42, Line 42, please delete "or Y and Z can" and replace with -- or X and Y can --

Claim 9, Column 43, Line 37, please delete "or phamiaceutically" and replace with -- or pharmaceutically --

Claim 21, Column 46, Line 32, please delete "founic acid" and replace with -- formic acid --

Claim 22, Column 46, Line 57, please delete "(i) foamable" and replace with -- (i) a foamable --

Claim 22, Column 47, Line 25, please delete "cyclic $C_i$–$C_{25}$" and replace with -- cyclic $C_1$–$C_{25}$ --

Claim 22, Column 47, Line 37, please delete "cyclic $C_i$–$C_{25}$" and replace with -- cyclic $C_1$–$C_{25}$ --

Signed and Sealed this  
Fifteenth Day of March, 2011

David J. Kappos  
*Director of the United States Patent and Trademark Office*